(12) United States Patent
Kukla et al.

(10) Patent No.: US 10,588,679 B2
(45) Date of Patent: Mar. 17, 2020

(54) COMPRESSION FIXATION SYSTEM

(71) Applicants: NUMAGENESIS, LLC, Hickory, NC (US); Robert Kukla, Hickory, NC (US); Marc Von Amsberg, Waxhaw, NC (US); Lawrence Binder, Miami, FL (US)

(72) Inventors: Robert Kukla, Hickory, NC (US); Marc Von Amsberg, Waxhaw, NC (US); Lawrence Binder, Miami, FL (US)

(73) Assignee: NUMAGENESIS, LLC, Hickory, NC (US)

(*) Notice: Subject to any disclaimer, the term of this patent is extended or adjusted under 35 U.S.C. 154(b) by 232 days.

(21) Appl. No.: 15/521,742

(22) PCT Filed: Nov. 2, 2015

(86) PCT No.: PCT/US2015/058670
§ 371 (c)(1),
(2) Date: Apr. 25, 2017

(87) PCT Pub. No.: WO2016/070191
PCT Pub. Date: May 6, 2016

(65) Prior Publication Data
US 2017/0238983 A1    Aug. 24, 2017

Related U.S. Application Data

(60) Provisional application No. 62/073,968, filed on Nov. 1, 2014.

(51) Int. Cl.
*A61B 17/88* (2006.01)
*A61B 17/68* (2006.01)

(52) U.S. Cl.
CPC ............ *A61B 17/885* (2013.01); *A61B 17/68* (2013.01); *A61B 17/683* (2013.01);
(Continued)

(58) Field of Classification Search
CPC ....... A61B 17/68; A61B 17/683; A61B 17/88; A61B 17/885; A61B 17/8866; A61B 17/8869; A61B 17/8872
See application file for complete search history.

(56) References Cited

U.S. PATENT DOCUMENTS

| 2,485,531 A | 10/1949 | Dzus William |
| 5,190,543 A | 3/1993 | Schlapfer |

(Continued)

FOREIGN PATENT DOCUMENTS

| DE | 4103494 C1 | 4/1992 |
| EP | 3258868 | 12/2017 |

(Continued)

OTHER PUBLICATIONS

Cachia, V.V., et al., Mechanical Characteristics of the New BONE-LOK Bi-Cortical Internal Fixation Device, Nov./Dec. 2003, 344-349, vol. 42, No. 6, The Journal of Foot & Ankle Surgery, California.

(Continued)

*Primary Examiner* — Eric S Gibson
(74) *Attorney, Agent, or Firm* — McNees Wallace & Nurick LLC

(57) ABSTRACT

The invention is directed in various aspects to a compression fixation system that includes coupling components and locking assemblies for connecting two or more separate elements in a fixed arrangement. For example, the system is useful for connecting and compressing two or more elements selected from bones and bone fragments. The system includes a substantially linear coupling component, such as, (Continued)

for example, a Kirschner Wire ("K-Wire") and locking assembly elements that engage with the coupling component in a coaxial orientation. The coupling component includes at least a linear portion and an anchor portion, the anchor portion configured to be fixed within or adjacent to a first one of the elements to be connected and the linear portion configured to be fixed adjacent to a second one of the elements to be connected, where the locking assembly is attached coaxially with and locked against the second element to achieve compression and fixation.

24 Claims, 20 Drawing Sheets

(52) U.S. Cl.
CPC ...... *A61B 17/8866* (2013.01); *A61B 17/8869* (2013.01); *A61B 17/8872* (2013.01)

(56) References Cited

U.S. PATENT DOCUMENTS

| | | | |
|---|---|---|---|
| 5,409,486 A | 4/1995 | Reese | |
| 5,613,968 A | 3/1997 | Lin | |
| 5,797,963 A | 8/1998 | McDevitt | |
| 5,814,071 A | 9/1998 | McDevitt et al. | |
| 5,851,189 A | 12/1998 | Forber | |
| 5,871,504 A | 2/1999 | Eaton et al. | |
| 5,931,840 A | 8/1999 | Goble et al. | |
| 5,947,967 A | 9/1999 | Barker | |
| 6,162,234 A * | 12/2000 | Freedland | A61B 17/0401 411/344 |
| 6,206,895 B1 | 3/2001 | Levinson | |
| 6,319,263 B1 | 11/2001 | Levinson | |
| 6,622,731 B2 | 9/2003 | Daniel et al. | |
| 6,673,078 B1 | 1/2004 | Muncie | |
| 6,685,705 B1 | 2/2004 | Taylor | |
| 6,706,045 B2 | 3/2004 | Lin et al. | |
| 6,860,889 B2 | 3/2005 | Bonati et al. | |
| 6,872,209 B2 | 3/2005 | Morrison | |
| 6,887,243 B2 | 5/2005 | Culbert | |
| 6,984,241 B2 | 1/2006 | Lubbers et al. | |
| 6,994,725 B1 | 2/2006 | Goble | |
| 7,083,622 B2 | 8/2006 | Simonson | |
| 7,172,595 B1 | 2/2007 | Goble | |
| 7,270,665 B2 | 9/2007 | Morrison et al. | |
| 7,326,211 B2 | 2/2008 | Padget et al. | |
| 7,485,119 B2 | 2/2009 | Thelen et al. | |
| 7,517,350 B2 | 4/2009 | Weiner et al. | |
| 7,563,275 B2 * | 7/2009 | Falahee | A61B 17/1757 606/104 |
| 7,578,833 B2 | 8/2009 | Bray | |
| 7,591,838 B2 | 9/2009 | Kramer et al. | |
| 7,641,677 B2 | 1/2010 | Weiner et al. | |
| 7,824,429 B2 * | 11/2010 | Culbert | A61B 17/7064 606/279 |
| 7,967,820 B2 | 6/2011 | Bonutti et al. | |
| 7,981,143 B2 * | 7/2011 | Doubler | F16B 37/0864 606/300 |
| 8,080,016 B2 | 12/2011 | Moorcroft et al. | |
| 8,128,627 B2 | 3/2012 | Justin et al. | |
| 8,287,538 B2 | 10/2012 | Brenzel et al. | |
| 8,303,598 B2 | 11/2012 | Frankel et al. | |
| 8,702,768 B2 | 4/2014 | Tipirneni | |
| 8,715,284 B2 | 5/2014 | Culbert | |
| 8,828,067 B2 | 9/2014 | Tipirneni et al. | |
| 10,151,337 B2 * | 12/2018 | Hill | F16B 21/00 |
| 2001/0025181 A1 | 9/2001 | Freedlan | |
| 2002/0133148 A1 | 9/2002 | Daniel et al. | |
| 2003/0088270 A1 | 5/2003 | Lubbers et al. | |
| 2003/0149436 A1 * | 8/2003 | McDowell | A61B 17/68 606/916 |
| 2004/0024420 A1 | 2/2004 | Lubbers et al. | |
| 2004/0030339 A1 | 2/2004 | Wack et al. | |
| 2004/0068269 A1 | 4/2004 | Bonati et al. | |
| 2004/0097941 A1 | 5/2004 | Weiner et al. | |
| 2005/0053423 A1 * | 3/2005 | Doubler | F16B 37/0864 403/374.3 |
| 2005/0096508 A1 | 5/2005 | Valentini et al. | |
| 2005/0177166 A1 | 8/2005 | Timm et al. | |
| 2005/0216007 A1 | 9/2005 | Woll et al. | |
| 2005/0228382 A1 | 10/2005 | Richelsoph et al. | |
| 2007/0010816 A1 | 1/2007 | Wilkinson et al. | |
| 2007/0010821 A1 | 1/2007 | Wilkinson et al. | |
| 2007/0162026 A1 | 7/2007 | Tipirneni et al. | |
| 2007/0233100 A1 | 10/2007 | Metzinger | |
| 2007/0233101 A1 | 10/2007 | Metzinger | |
| 2007/0233102 A1 | 10/2007 | Metzinger | |
| 2007/0233103 A1 | 10/2007 | Metzinger | |
| 2007/0233104 A1 | 10/2007 | Metzinger | |
| 2007/0260248 A1 | 11/2007 | Tipirneni | |
| 2007/0270833 A1 | 11/2007 | Bonutti et al. | |
| 2008/0108996 A1 | 5/2008 | Padget et al. | |
| 2008/0147127 A1 | 6/2008 | Tipirneni et al. | |
| 2008/0195122 A1 | 8/2008 | Castellvi et al. | |
| 2008/0300606 A1 | 12/2008 | Moorcroft et al. | |
| 2008/0319266 A1 | 12/2008 | Poll et al. | |
| 2009/0048606 A1 | 2/2009 | Tipirneni et al. | |
| 2009/0118773 A1 | 5/2009 | James et al. | |
| 2009/0131936 A1 | 5/2009 | Tipirneni et al. | |
| 2009/0131990 A1 | 5/2009 | Tipirneni et al. | |
| 2009/0131991 A1 | 5/2009 | Tipirneni et al. | |
| 2009/0216232 A1 | 8/2009 | Buford et al. | |
| 2009/0228007 A1 | 9/2009 | Justin et al. | |
| 2009/0228008 A1 | 9/2009 | Justin et al. | |
| 2009/0254089 A1 | 10/2009 | Tipirneni et al. | |
| 2009/0254129 A1 | 10/2009 | Tipirneni et al. | |
| 2010/0121326 A1 | 5/2010 | Woll et al. | |
| 2010/0312292 A1 | 12/2010 | Tipirneni et al. | |
| 2011/0098755 A1 | 4/2011 | Jackson et al. | |
| 2011/0125189 A1 * | 5/2011 | Stoll, Jr. | A61B 17/0401 606/232 |
| 2011/0137356 A1 * | 6/2011 | Kollmer | A61B 17/683 606/324 |
| 2011/0196380 A1 | 8/2011 | Cremer et al. | |
| 2011/0295252 A1 | 12/2011 | Tipirneni et al. | |
| 2011/0295253 A1 | 12/2011 | Bonutti et al. | |
| 2012/0083742 A1 | 4/2012 | Nelson | |
| 2012/0226326 A1 | 9/2012 | Overes et al. | |
| 2012/0245630 A1 * | 9/2012 | Napolitano | A61B 17/0401 606/232 |
| 2012/0253410 A1 | 10/2012 | Taylor et al. | |
| 2013/0012954 A1 | 1/2013 | Paroth et al. | |
| 2013/0079776 A1 | 3/2013 | Zwirkoski et al. | |
| 2013/0110168 A1 | 5/2013 | McCormack et al. | |
| 2013/0158560 A1 | 6/2013 | Gleason et al. | |
| 2013/0238036 A1 | 9/2013 | Sinha | |
| 2014/0243828 A1 * | 8/2014 | Heiney | A61B 17/1728 606/70 |
| 2014/0257419 A1 | 9/2014 | Arthur et al. | |
| 2017/0238983 A1 * | 8/2017 | Kukla | A61B 17/68 |

FOREIGN PATENT DOCUMENTS

| | | |
|---|---|---|
| FR | 2831419 A1 | 5/2003 |
| WO | WO1997030649 A1 | 8/1997 |
| WO | WO1998012972 A1 | 4/1998 |
| WO | WO1999011177 A2 | 3/1999 |
| WO | WO2001049189 A1 | 7/2001 |
| WO | WO2001049207 A2 | 7/2001 |
| WO | WO2001095818 A1 | 12/2001 |
| WO | WO2004045373 A3 | 5/2005 |
| WO | WO2007010185 A1 | 1/2007 |
| WO | WO2009091811 A1 | 7/2009 |
| WO | WO2009143374 A2 | 11/2009 |
| WO | WO2010034002 A1 | 3/2010 |
| WO | WO2010048473 A1 | 4/2010 |
| WO | WO2010091242 A1 | 8/2010 |
| WO | WO2010093590 A1 | 8/2010 |

(56) References Cited

FOREIGN PATENT DOCUMENTS

WO  WO2010096724 A1  8/2010
WO  WO2012024465 A2  2/2012

OTHER PUBLICATIONS

Notification of Transmittal of the International Search Report and the Written Opinion of the International Searching Authority, or the Declaration for corresponding application PCT/US2019/030654, filed May 3, 2019.

* cited by examiner

COMPRESSION FIXATION SYSTEM

RELATED APPLICATIONS

This application is a 35 USC 371 National Stage application that claims priority to PCT/US2015/058760 filed on Nov. 2, 2015, which application claims the benefit under 35 U.S.C. § 119 (e) to U.S. Provisional Application Ser. No. 62/073,968 filed Nov. 1, 2014, the entireties of which are incorporated herein by reference.

FIELD OF INVENTION AND BACKGROUND

The invention relates generally to a locking assembly and a compression fixation system for fixing two or more elements together and to maintain, and optionally adjust a desired degree of compression across the two or more objects. The system is suitable, for example, for connecting and compressing two or more elements selected from bones and bone fragments. The system includes a substantially linear coupling component, and a locking assembly that engages with a locking assembly-receiving portion the coupling component in a generally coaxial orientation.

The invention is described herein below in relation to bone fractures, which is but an example of the useful application of the invention. One skilled in the art will appreciate that the locking assembly and compression fixation system components and the methods of use thereof as described herein can be used without undue adaptation for applications that include, but are not limited to: connecting one or more medical devices or appliances to bone; connecting one or more medical or other devices together; repairing structural components, for example, household, building and construction components such as combinations of two or more pieces of wood, concrete, supports, beams, studs, joists, columns, wall boards; and the like.

Devices and systems as disclosed herein are useful for a variety of applications, including with particularity, orthopedic fixation. There are many needs in orthopedics for the fixation of bones. In some instances, adjacent bones must be fixed together to allow for healing of damaged associated soft tissue, or to replace the function of such soft tissue, such as in the case of ligament damage between adjacent bones as well as tendon damage. In other instances, fractures of bones must be corrected by alignment, reduction of space between, and compression of the bone fragments to enable bone healing. Many approaches are known in the medical arts for achieving the attachment, fixation, and desired degrees of compression of bones and bone fragments. Generally, for example, threaded screws with and without heads, pins and rods, and wires may be used. There are challenges with all of these, which include, for example, imprecise compression and fixation, protrusion of the fixation element from bone into tissue (screw heads, twists of wires), bone loss/damage due to size of fixation element and damage to bone (for example, thread stripping of screws within bone), and costs associated with inventory to provide the number of components needed to meet size ranges of fractures.

Included in the art are several examples of compression bone fixation systems that are aimed at overcoming the shortcomings of wires and screws for bone fixation. In many instances, such systems provide fixation that overcomes some of the limitations of bone screws and wires. However, it remains a problem in the art to achieve fixation of relatively small bones using low profile fixation components that are capable of fine adjustment to placement and tensioning, are relatively simple to manipulate and are adjustable and/or removable post fixation.

Accordingly, there is a need for a fixation system that can fix, align and compress bone elements together wherein the system presents minimal risk of bone compromise and loss, and provides ease of use by the clinician, adjustability in size to minimize inventory needs, and highly reliable and precise and reversible locking to achieve reliable fixation and enable the clinically needed degree of compression between bone elements. Indeed, a particular advantage of the inventions provided herein is overcoming the challenges presented in the art with implant placement and subsequent adjustment or removal.

BRIEF DESCRIPTION OF THE DRAWINGS

Features and advantages of the general inventive concepts will become apparent from the following description made with reference to the accompanying drawings, including drawings represented herein in the attached set of figures, of which the following is a brief description.

Figure 1:
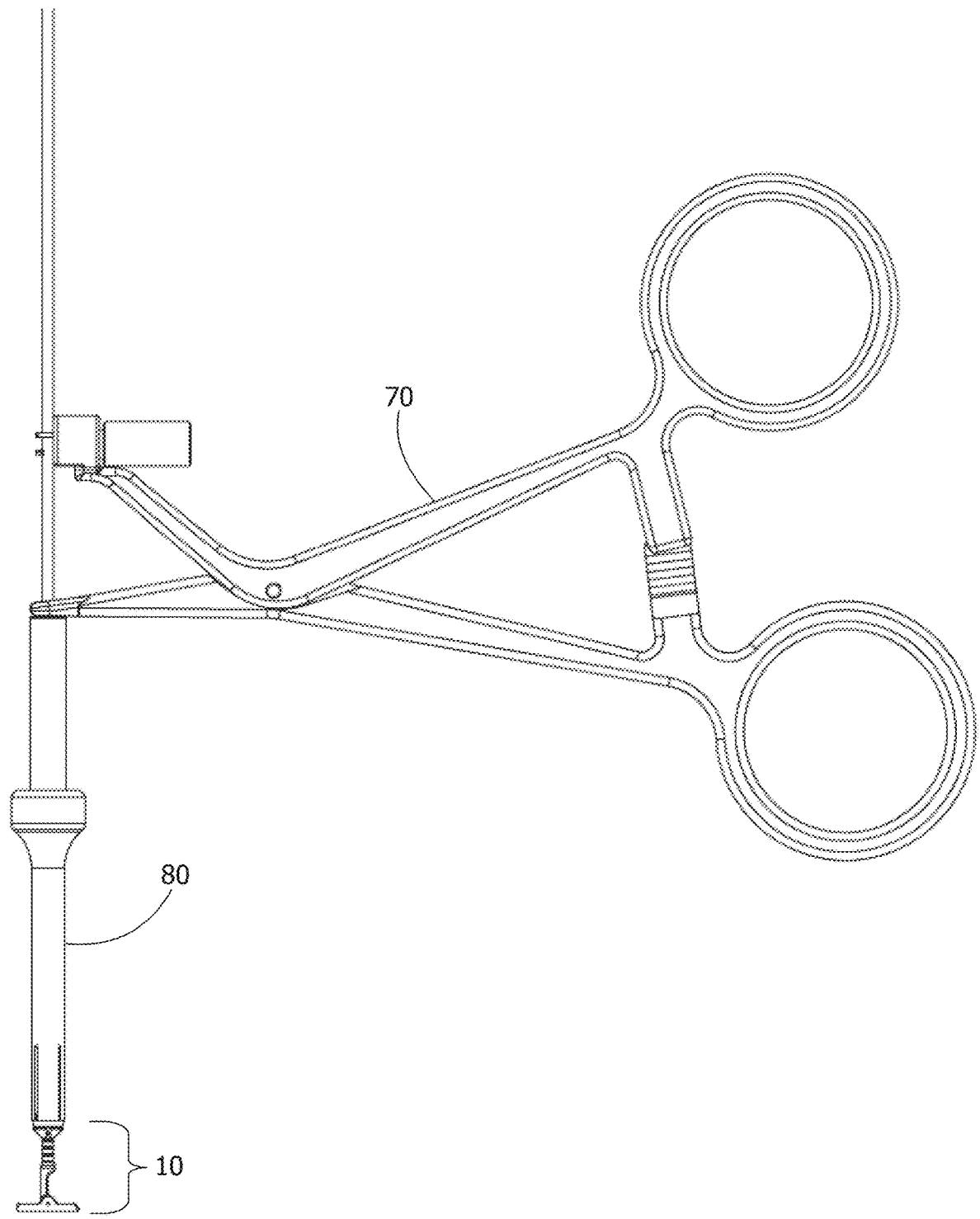
FIG. 1 shows a side view of a first embodiment of a fully assembled compression fixation system engaged with coupling component tensioning and insertion tools.

Features and advantages of the general inventive concepts will become apparent from the following description made with reference to the accompanying drawings, including drawings represented herein in the attached set of figures, of which the following is a brief description:

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DESCRIPTION

This description describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

The general inventive concepts will now be described with occasional reference to the exemplary embodiments of the invention. Unless otherwise defined, all technical and scientific terms used herein have the same meaning as commonly understood by one of ordinary skill in the art encompassing the general inventive concepts. The terminology set forth in this detailed description is for describing particular embodiments only and is not intended to be limiting of the general inventive concepts.

As used herein, the singular forms "a," "an," and "the" are intended to include the plural forms as well, unless the context clearly indicates otherwise. The term "proximal" as used in connection with any object refers to the portion of the object that is closest to the operator of the object (or some other stated reference point), and the term "distal" refers to the portion of the object that is farthest from the operator of the object (or some other stated reference point). The term "operator" means and refers to any professional or paraprofessional who delivers clinical care to a medical patient, particularly in connection with the delivery of care. More broadly, in connection with non-medical uses of the inventions described herein, the term refers to a user of one or more components of the compression fixation system.

Unless otherwise indicated, all numbers expressing quantities, properties, and so forth as used in the specification and claims are to be understood as being modified in all instances by the term "about." Accordingly, unless otherwise indicated, the numerical properties set forth in the specification and claims are approximations that may vary depending on the suitable properties desired in embodiments of the present invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

Use of Compression Fixation System

Generally in accordance with the embodiments described herein and depicted in the drawings, the invention is directed in various aspects to systems, components, instruments, and methods for fixing and/or compressing elements along a generally rectilinear path, using at least one of each of a coupling component and a locking assembly. As described herein, the locking assembly and the coupling component engage in a generally coaxial orientation, such that, at least a portion of the coupling component comprises a generally rectilinear configuration and is adapted to engage with the locking assembly.

In certain particular embodiments, the system enables fixation of two or more traumatized, fractured, deformed, and/or otherwise displaced bones or bone fragments. Embodiments of compression fixation systems are disclosed herein that significantly enhance the surgical techniques for repairing damaged bones, such as fractured phalangeal and metatarsal bones, and provide improved and superior performance in the achievement and maintenance of fixation and desired bone compression as compared with use of conventional wires and screws. For example, in contrast to screws, certain embodiments of the systems described herein enable flexible and adjustable orientation and positioning of adjacent bones to be fixed, which cannot be achieved using conventional rigid screws. In particular, the adaptable sizing of the coupling components enables customized sizing without the need to have a wide array of sizes on hand such as is required when using screws. That is, the coupling components are adaptable for use with different locking assemblies, and the coupling components can be adjusted in a length dimension, thus obviating the need for alternate lengths. And in another example, in contrast to conventional K (Kirschner) wires which are also used in the medical arts for bone fixation whereby they are fixed into compression via crimping and twisting, certain embodiments of the systems described herein enable precise compression that can be finely and selectively adjusted without compromise to the healing bone or to the fixation system components. Moreover, the instant disclosure enables use of ancillary fixation devices such as flanges and plates that can be positioned and locked to bone using the adjustable locking assemblies described herein.

Significant benefits can be realized in connection with surgical use of the fixation system, including, but not limited to: optimized patient experience and outcome as a result of controlled and precise compression to enhance healing and minimized bone damage/loss; improved time efficiency during surgery; and enhanced options for implant selection and customization. Time savings during surgery are realized in comparison to the current state of the art due to the elimination of need to precisely measure for and select a specific length of implant; the instant disclosure provides a system that can be customized in size without any compromise in fixation. Cost savings can also be realized through reduction of required implant sizes; the instant disclosure provides a system in which one implant fits all and can be easily sized to the specific patient, resulting in a significant reduction in the number and size of devices that must be stocked.

While the examples provided herein pertain to the fixation/compression of bone material, it will be appreciated that other materials of relevance to the body, including biological and non-biological, implanted and non-implanted, can be fixed together and as desirable, compressed using the inventions disclosed herein. Examples herein include use of the compression fixation system for reduction, alignment, fixation and/or compression of bone fragments such as in the phalanges and metatarsal bones. Of course, it will be appreciated by one skilled in the art that the inventive components can be used in connection with most types of fractures, particularly such fractures that are typically treated by percutaneous insertion of pins and wires and screws. Further, the system is suitable for use with other bone element fixation indications.

Components, Instruments and Techniques for Compression/Fixation

Example 1: Snap Fit Compression Fixation System 10

Referring now to the drawings, FIG. 1 shows a side view of a fully assembled compression fixation system 10 engaged with coupling component 20 tensioning and locking assembly 40 insertion instruments 70, 80.

The compression fixation system 10 includes a coupling component 20 that is selected from suitable wire and other bone pins and similar rod type devices, such as, for example K-wire. The coupling component 20 is adapted at a distal first end 21, intended to be most distal to the operator, with an anchor portion 23 for fixation within or on a distal outer surface of a first bone element. The coupling component 20 is further adapted at a proximal second end 22, intended to be most proximal to the operator, with a locking assembly 40 receiver portion 24 that is generally rectilinear. In various embodiments, at least the proximal second end 22 portion of the coupling component 20 is substantially rectilinear, and cylindrical, while the distal and a medial portion of the coupling component 20 may be other than rectilinear or may be initially rectilinear and manipulated by the operator for optimal engagement and shape conformity with the two or more elements to be fixed.

The distal anchor portion 23 of the coupling component 20 may be selected from any of a number of anchors known in the art, and generally selected from (i) those that are adapted to engage with and remain substantially within and anchor to a bone, and (ii) those that extend through bone and are adapted to engage with an outer surface of a bone or bone fragment, or a plate or other non-bone material that is intended to be held adjacent to the distal bone element. Some examples of anchors that are adapted to engage with and remain substantially within and anchor to a bone include self or non-self tapping threads, and bone engagement features that can engage by press fitting such as keels, ribs and fins. Some examples of anchors that extend through bone and are adapted to engage with an outer surface include coils, barbs, and toggles.

Figure 2:
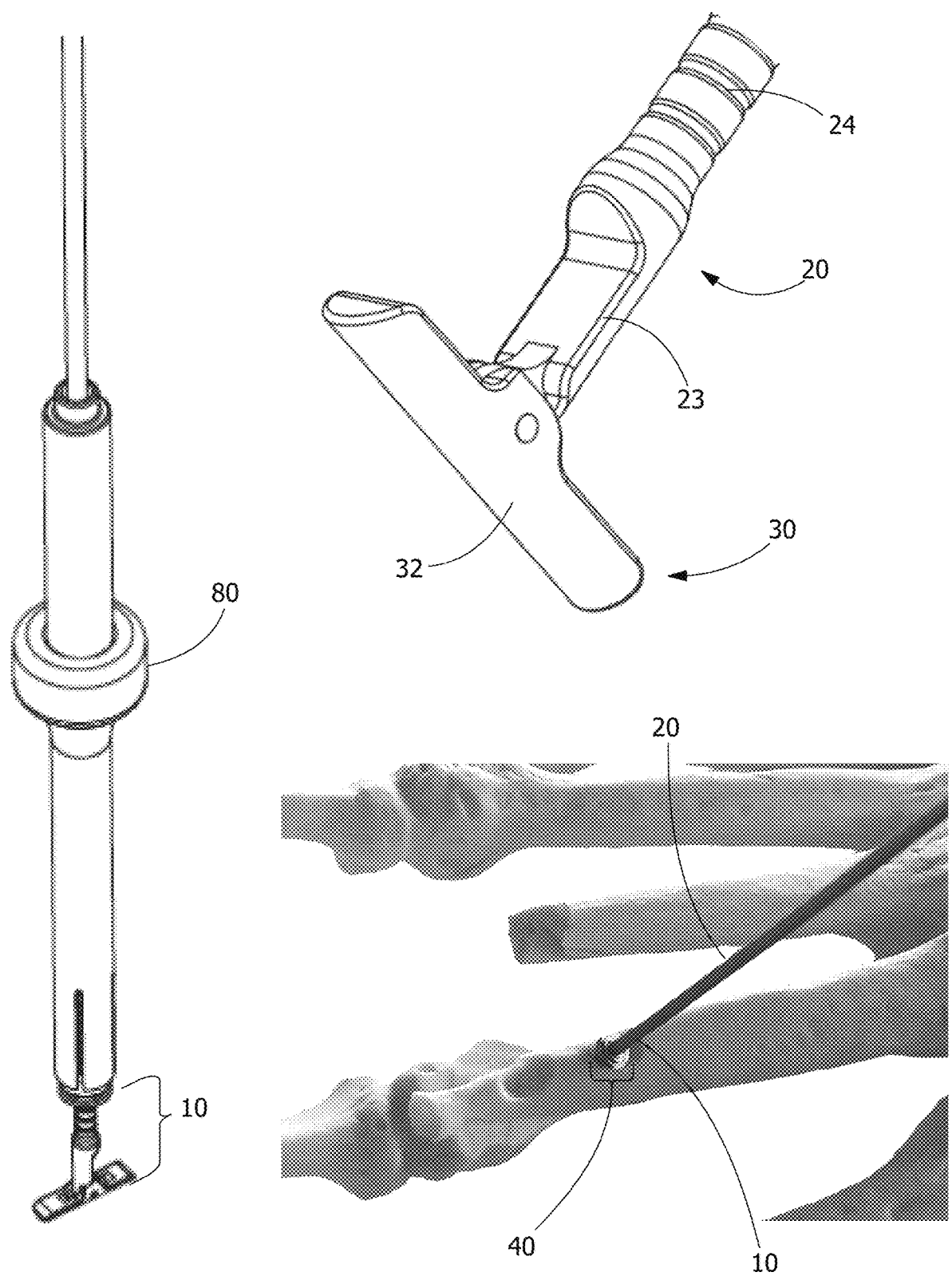
FIG. 2 shows in the left panel an enlarged perspective view of an embodiment of a fully assembled compression fixation system engaged with coupling component locking assembly insertion tools, and in the upper right panel a close up perspective view of respective embodiments of a coupling component, and in the lower right panel an anchor and an anatomically correct model of a foot with a metatarsal fracture that is fixated with an embodiment of a compression fastening system according to this disclosure.

Referring now to FIG. 2, an anatomically correct model of a foot with a metatarsal fracture is shown, wherein the fracture is fixated with an embodiment of a compression fixation system 10 according to this disclosure. As shown, an untrimmed coupling component 20 extends proximally out of the upper surface of the fractured bone, and a locking assembly 40 is fixed on the coupling component 20 and is in compression against the proximal (upper) bone element while the anchor (not shown) is oriented opposite from the locking assembly 40 on the distal side of the distal (lower) bone fragment to achieve locked fixation between the bones.

One of ordinary skill will appreciate that the depicted coupling component 20 can be provided in variable lengths, with or without curves or bends, with or without surface texture and/or surface features. Moreover, while the depicted coupling component 20 is generally cylindrical in shape from the proximal end and terminates at the exemplary anchor, one of ordinary skill will appreciate that the shape may be other than cylindrical (i.e., the cross section may be other than circular). Thus, in some alternate embodiments, the coupling component 20 may have a cross section that is selected from one of the following non-limiting examples, including, scalloped, star shaped, hexagonal, square, and ovoid. Likewise, the coupling component 20 may be uniform in cross sectional shape and width along its entire length, or it may comprise regions that vary and include combinations of different cross sectional shapes, widths/diameters, and textures.

Thus, it will be appreciated that any particular portion of a coupling component 20 which may be substantially rectilinear for receiving a locking assembly 40 may be cylindrical or otherwise shaped and may be smooth or have any one of a variety of surface features 26 such as grooves or notches and textures that comprise knurling or other non-smooth texturing. Further, while the exemplary embodiment of the coupling component 20 shown in the drawings terminates as a cylinder at the proximal end, there may be alternate shapes and features at the proximal end that are suited for engagement with a tool or instrument. Thus, in some non-limiting examples, the coupling component 20 may comprise at its proximal end a hemispherical, conical or frustoconical feature, or a star, scallop or hex cross-section, or combinations of these.

Figure 3:
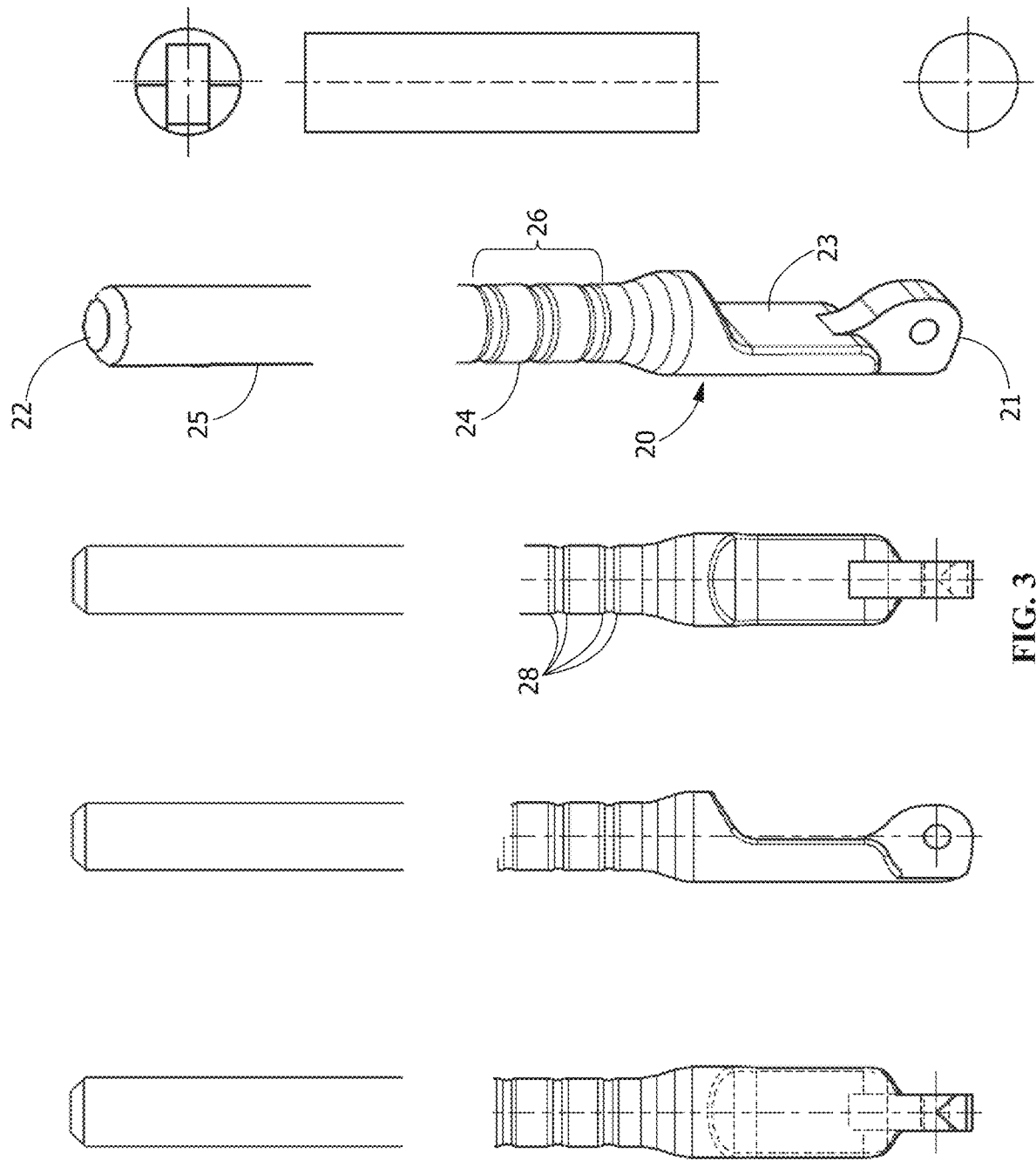
FIG. 3 shows alternate front, side, back, perspective, bottom, side and top views of an embodiment of a coupling component.
Figure 4:
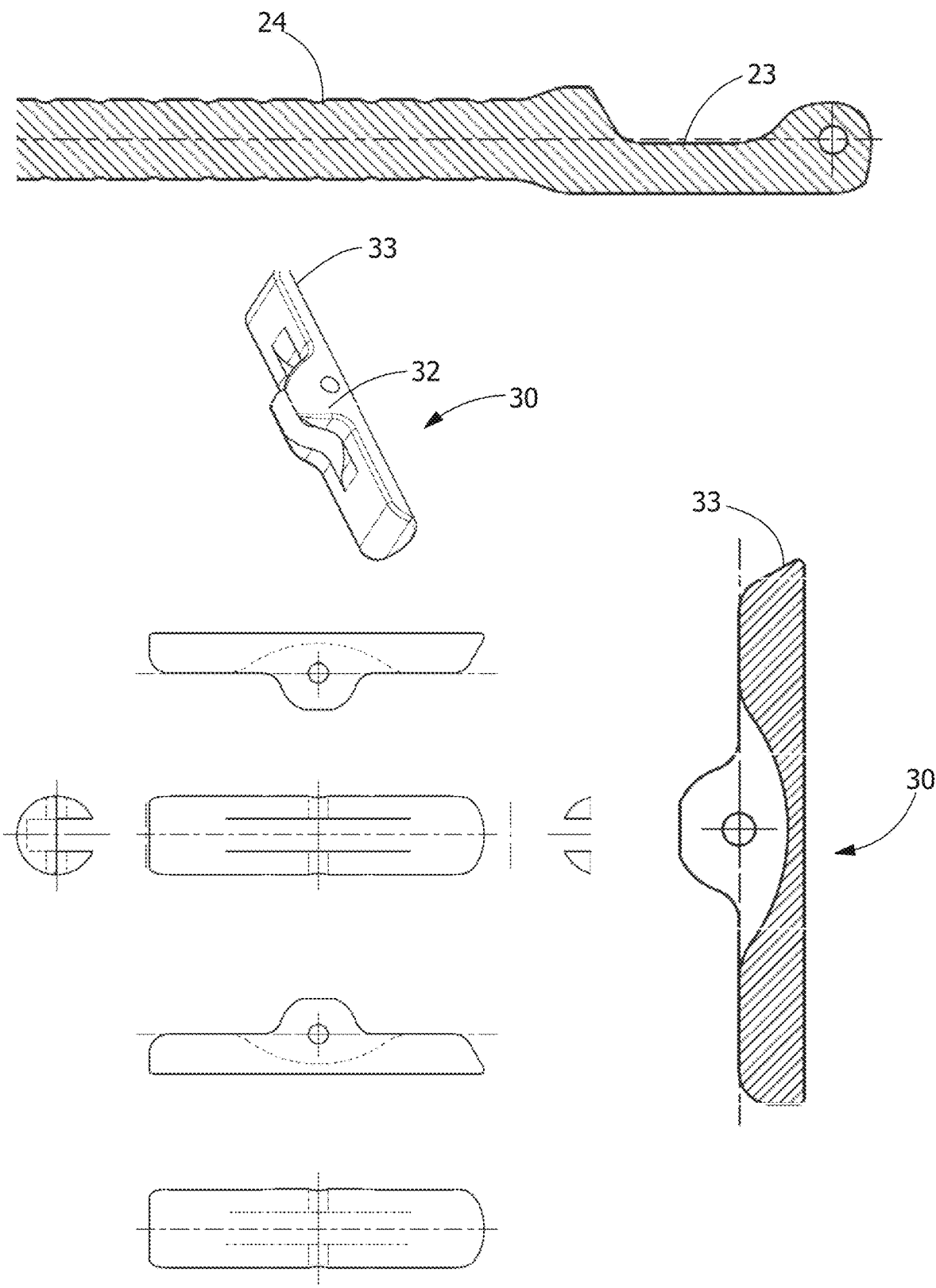
FIG. 4 shows in the upper left panel alternate front, bottom, side, top, side, perspective and end views of the embodiment of the anchor shown in FIG. 2 the anchor comprising a toggle, and in the bottom left and right panels, respectively, cross sectional side views of respective embodiments of the anchor and coupling component.

Referring now to FIG. 3, alternate views of an embodiment of a coupling component 20 are shown, and in FIG. 4 cross sectional views of the distal first end 21 portion of a coupling component 20 and a detached toggle anchor 30 are shown. In the depicted embodiment, the coupling component 20 comprises a series of spaced circumferential grooves along at least a portion of its length, the grooves adapted for receiving one or more ridge features on the inner surface of a locking assembly 40. It will be appreciated that in some embodiments, the number and spacing of the grooves may vary such that there are more or fewer, the grooves are narrower or wider, deeper or shallower, and are equidistant or variably spaced. In addition, in alternate embodiments, a coupling component 20 may comprise other surface features 26 to either enhance sliding between a coupling component 20 or to enhance friction there between. Further, such textures and features may vary along the length of a coupling component 20 to differentially enhance surface contact with various instruments, collet compression locking components, and bone.

In some alternate embodiments, the coupling component 20 may have a diameter that permits cannulation through at least a portion of the coupling component 20. In some examples such embodiments would include cannulated bone wires and pins. In other such embodiments, examples include tubes, conduit, pipes, and other substantially hollow components that are suitable to receive a locking assembly 40 along at least a portion of the component that is rectilinear.

Referring again to the drawings, enlarged views of the distal first end 21 portion of an exemplary embodiment of a coupling component 20 are shown in FIG. 2. As depicted, the anchor is a toggle anchor 30, which is pivotal around an axis that is perpendicular to a long axis of the coupling component 20. In the depicted embodiment, the toggle anchor 30 is pivotal in only one direction, the coupling component 20 being adapted to receive the toggle anchor 30 into a recess 27 that receives a portion of the toggle anchor 30 body 32 whereby the overall cross sectional area of the distal end 33 of the closed toggle anchor 30 matches the cross sectional area of the distal portion of the coupling component 20 allowing a minimal profile for insertion into bone. The cantilever design enables actuation of the toggle anchor 30 against tissue that is distal to the most distal bone fragment to facilitate engagement of the toggle anchor 30 with the bone for achieving fixation between the bone fragments. Of course, it will be appreciated that other mating configurations of a toggle anchor 30 and coupling component 20 are possible.

Referring to FIG. 2, the left panel shows a proximal to distal end perspective view of the assembly including insertion instruments with a toggle anchor 30 at the distal end, and FIG. 2 upper right panel shows a close up alternate distal to proximal end perspective view of a deployed toggle anchor 30. In each of FIG. 1 and FIG. 2 the toggle anchor 30 is in a securement configuration, such that the toggle anchor 30 is pivoted so that it is aligned perpendicular to the long axis of the coupling component 20 to enable securement against bone through which the assembly is passed. In the insertion configuration (not shown) the toggle anchor 30 is pivoted 90 degrees so that its axis is in line with the axis of the proximal end of the coupling component 20, for insertion into the bone and allowing clean exit from a hole in the bone that traverses the bone from a proximal to a distal end of the bone.

Actuation of the pivot feature of the toggle anchor 30 rotates its position so that it is perpendicular to the axis of the coupling component 20, and is deployed to operate as an anchor, thereby preventing back out of the coupling component 20 from the bone. According to the instant embodiment shown in FIG. 2, the toggle anchor 30 as shown attaches to and engages with the coupling component 20 in a nested cantilever configuration, whereby actuation to close the toggle anchor 30 involves pivoting around a central pivot axis that is on the terminal end along the axis of the coupling component 20. In alternate embodiments as disclosed herein, the toggle anchor 30 component is attached in an alternate manner whereby the coupling component 20 is split at its end, and the toggle anchor 30 rotates within the split end of the coupling component 20. And in accordance with the depicted embodiment, the toggle anchor 30 is attached to the distal end of the coupling component 20 using a through pin 32 that snap fits or may alternatively be welded or soldered in place. One of ordinary skill will understand that yet in other embodiments, the toggle anchor 30 may be attached by any one of other possible means.

In various exemplary embodiments of the locking assembly 40, as shown in the drawings, inter-engaging compression and collet 50 components cooperate along a shared axis and inter-engage to form a locking assembly 40. Assembled locking assembly 40 components form a through channel for receiving a coupling component 20 to achieve locking fixation with the coupling component 20. According to the various embodiments, the compression and collet 50 components are constructed to slide over at least a distal first end 21 of the coupling component 20 while in an open configuration, can be held stably on the coupling component 20 in a friction (engaged but not locked) configuration to enable positioning relative to the elements to be fixed, and can be actuated to achieve a locked configuration.

Figure 5:
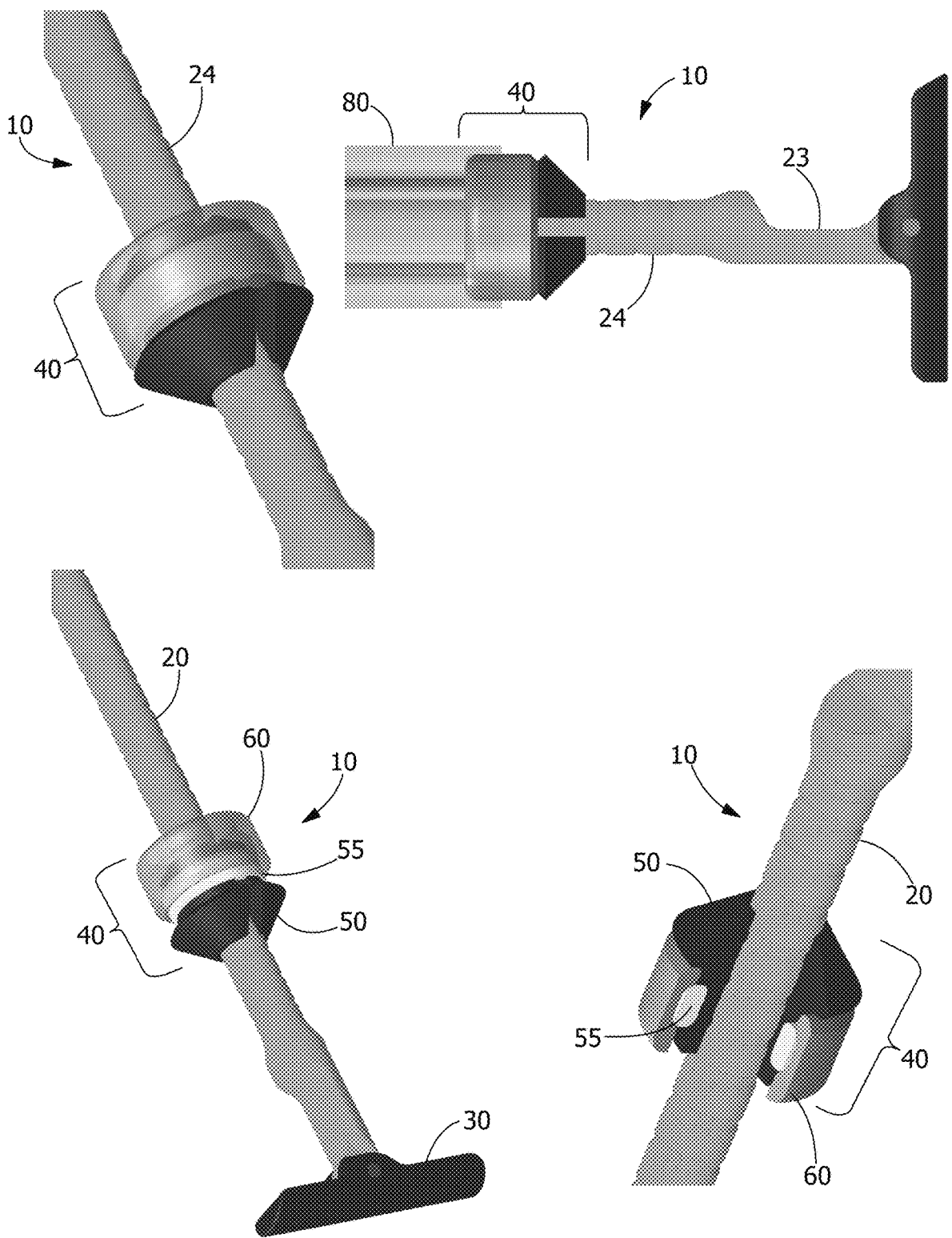
FIG. 5 shows in the upper left panel a close up perspective view in color of the compression fixation assembly in an open configuration, and in the upper right panel a close up of the locking assembly, and in the lower left panel an enlarged cutaway perspective view of a locking assembly in a locked configuration engaged with a coupling component of the compression fixation assembly, and in the lower right panel, an enlarged side view of the embodiment of a fully assembled compression fixation system engaged with coupling component locking assembly.

Referring again to the drawings, FIG. 5 shows an exemplary locking assembly 40 assembled with the coupling component 20 inserted through the central bore 52, the anchor in the form of a toggle anchor 30 in the open configuration for fixation to bone. The depicted embodiment of the locking assembly 40 comprises a collet 50, a securement ring 55, and a locking cap 60. As shown, the locking cap 60 is shown as transparent to reveal the relative interfitting between the respective collet 50, securement ring 55, and locking cap 60 components. FIG. 5 upper left panel shows the locking assembly 40 in an open configuration and FIG. 5 upper right panel shows the assembly in a locked configuration.

Figure 6:
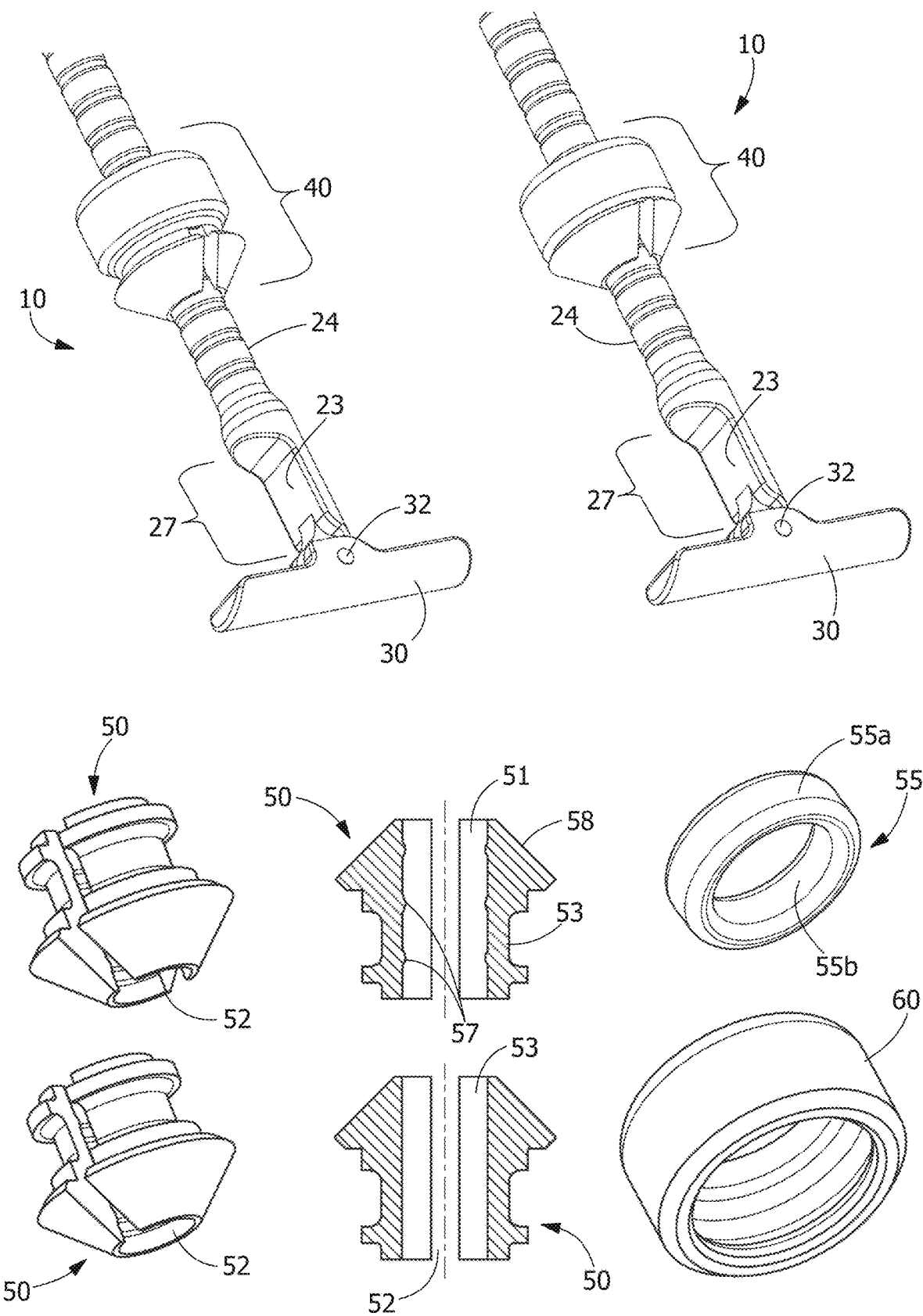
FIG. 6 shows in the upper left panel side views of alternate split and slit embodiments of locking collets, and in the middle left panel cross sectional side views of alternate smooth and textured embodiments of locking collets, and in the lower left panel an embodiment of a locking assembly cap on the left and an embodiment of a securement ring on the right; in the upper right and lower right panels, respectively, show alternate open and locked configuration views of the locking assembly embodiment.

Referring now to FIG. 6, the discrete collet 50, securement ring 55 and locking cap 60 components are shown, wherein with respect to each of the securement ring 55 and the locking cap 60, the components are shown with a perspective view from their proximal faces or tops, while with respect to the collet 50, it is shown with a perspective view from its distal face or bottom.

An advantageous aspect of this embodiment of the locking assembly 40 is that the connection and compression can be achieved without introduction of rotational insertion to the system; that is, the collet 50, securement ring 55 and locking cap 60 are designed to engage with the by compression and snap fitting, without rotating around the shared axis with the coupling component 20, thereby diminishing the risk of material stripping into patient tissue and ensuring optimal compression and purchase of the coupling component 20 surface. In various embodiments, the compression fixation system 10 may be provided for use by an operator in a pre-assembled state, completely disassembled, or in a state of sub-assembly.

Referring again to FIG. 6, alternate views of the locking assembly 40 are shown in the right panel, wherein in the top view the assembly is in an open configuration, and in the lower panel, the assembly is in a closed, locked configuration. As will be described further herein, the collet compression locking components are fully movable along the length of a coupling component 20 while in the open configuration. According to the instant embodiment, engagement of the securement ring 55 around the collet 50 provides sufficient force to maintain the collet 50 in a slightly compressed state, thereby allowing free movement of the provisionally engaged locking assembly 40 proximally and distally along the length of the coupling component 20. Applying axial compression to the locking assembly 40 results in the translation of the locking cap 60 distally, across the surface of the securement ring 55, whereby it encloses and compresses the securement ring 55 against the collet 50 to lock the assembly to the coupling component 20. In the closed configuration, the inner face of the collet 50 is compressed firmly against the coupling component 20 and this compressive force retains the position of the locking assembly 40 to maintain compression on the bone. According to the depicted embodiment as shown in FIG. 6, for example, the collet 50 is adapted with ridges on its inner face which are spaced and sized to inter-fit in corresponding circumferential grooves on the surface of the coupling component 20. In the closed configuration, the compression fit of the locking assembly 40 is enhanced through the inter-engagement between these ridges and grooves.

Of course, as described elsewhere herein, both the collet 50 and the coupling component 20 may be devoid of any surface features, wherein retention of the locking assembly 40 would rely on compressive force alone. And in other embodiments, one or more interacting surface features on either or both the collet 50 and the coupling component 20 may be provided to enhance locking. Notably, according to the embodiment shown in FIG. 6, when the locking assembly 40 is in the open configuration, the assembly can be adapted to move in either proximal or distal directions with the rounded ridges on the collet 50 passing over and across the rounded grooves on the coupling component 20 to enable precise positioning of the locking assembly 40 prior to closure. As such, at least in the depicted embodiments, the assembly can be freely adjusted without the use of any additional tools such as would be required with a one way ratcheting mechanism.

In the depicted embodiment of the collet 50, shown, for example, in FIG. 6, the collet 50, as depicted, is generally cylindrical, having a central bore 52 that is cylindrical and adapted to receive the coupling component 20, a tapered distal end that is generally frustoconical, a cylindrical proximal end, and is adapted in a center portion of its outer surface with a circumferential recess 53 adapted to receive and retain the securement ring 55. The locking cap 60 is adapted with internal engagement features to fit over and engage with the securement ring 55. In the open configuration, the distal opening of the locking cap 60 rests on and is provisionally secured to the securement ring 55. In the closed configuration, the locking cap 60 slides distally towards the distal end of the collet 50 and thereby encloses the securement ring 55 and engages with a distal end thereof to close the locking assembly 40.

Figure 7:
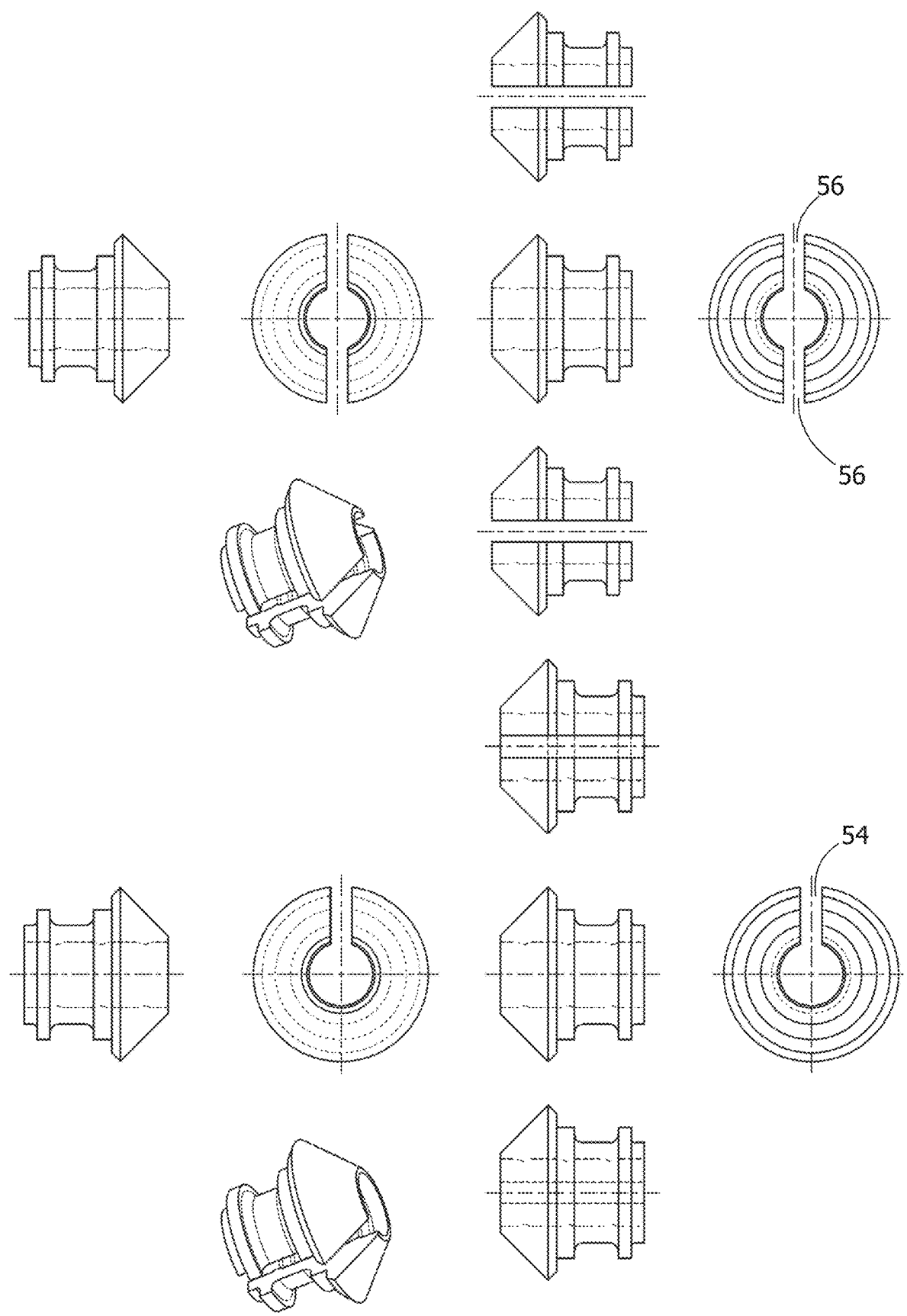
FIG. 7 shows in the left panel alternate front, perspective, top, side bottom, back, side, and bottom views of a split embodiment of a locking collet, and in the right panel alternate front, perspective, top, side bottom, back, side, and bottom views of a slit embodiment of a locking collet of the locking assembly.

Referring again to FIG. 6, the collet 50, as depicted, includes a generally frustoconical proximal end, with a central bore 52 that is substantially cylindrical from its proximal to its distal end. Referring to the upper left panel, two representative alternate embodiments of collet 50 are shown, wherein one embodiment is unitary with a single slit 54 from the proximal to the distal end. In another embodiment as show, the collet 50 is provided in two halves that are split 56 along the proximal to distal dimension. As shown in the lower left panel, a first embodiment of a collet 50 has a smooth cylindrical inner face 51, and a second embodiment has a textured inner face 51 comprising ridges 57. FIG. 7 left panel shows alternate views of a split collet 50, and FIG. 7 right panel shows alternate views of a split collet 50. It will be appreciated by one of ordinary skill that in some yet further embodiments, a collet 50 may be formed of more than two parts, and yet other embodiments of slit or slotted collets 50 may be provided. Some alternate slotting embodiments of collets 50 are described herein.

According to some embodiments, the collet 50 comprises a series of spaced circumferential ridges 57 along at least a portion of the length of its internal face 51 from proximal to distal, the ridges adapted for resting in one or more groove features 28 on the surface of a coupling component 20. It will be appreciated that in some embodiments, the number and spacing of the ridges 57 on the inner face of the collet 50 may vary such that there are more or fewer, the ridges are narrower or wider, sharper or shallower, and are equidistant or variably spaced. In addition, in alternate embodiments, a collet 50 may comprise no surface features on its internal face 51, other surface features or combinations thereof to either enhance sliding between a collet 50 and a coupling component 20 or to enhance friction there between. Further, such textures and features may vary along the internal face 51 of the collet 50 to differentially enhance surface contact with a coupling component 20. It will be appreciated by those skilled in the art that other engagement features are possible and that the disclosed engagement feature is not to be limiting. In alternate embodiments, all or a portion of the interior face 51 as well as the exterior surface 58 of the collet 50 may be textured by surface treatment or other features such as ridges 57, grooves, keels, fins, thread, dimples and the like to enhance engagement with and locking between the collet 50 and the coupling component 20.

Figure 19:
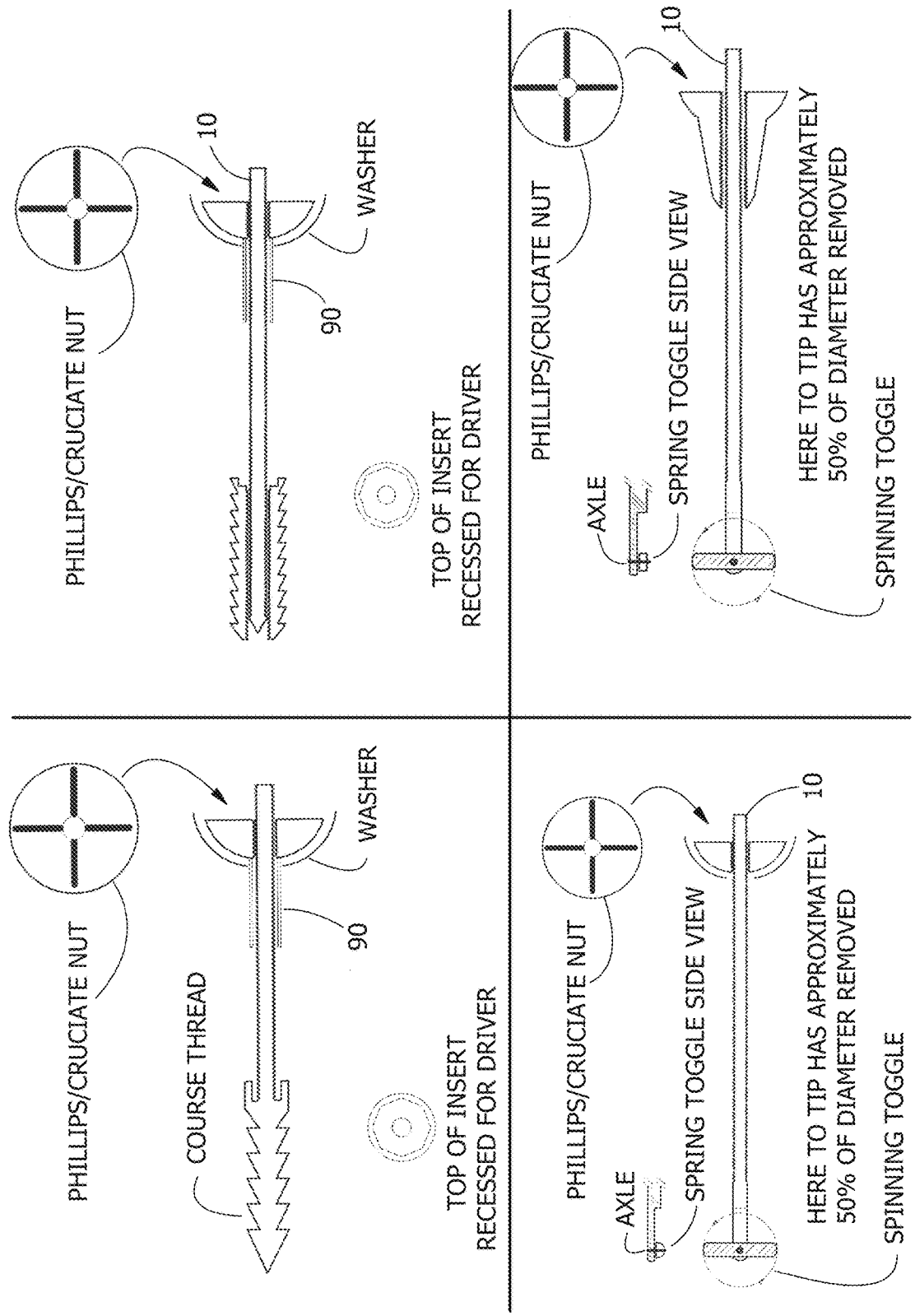
FIG. 19 depicts respectively in the upper left, upper right, lower left and lower right panels alternate embodiments a compression fixation system comprising an first end having a anchor and a second end having a locking compression means for securing and locking an elongate coupling component; and, FIG. 20 depicts respectively in the upper left and upper right panels alternate embodiments a compression fixation system comprising an first end having a anchor and a second end having a locking compression means for securing and locking an elongate coupling component, and in a lower panel an alternate embodiment of an anchor component.
Figure 20:
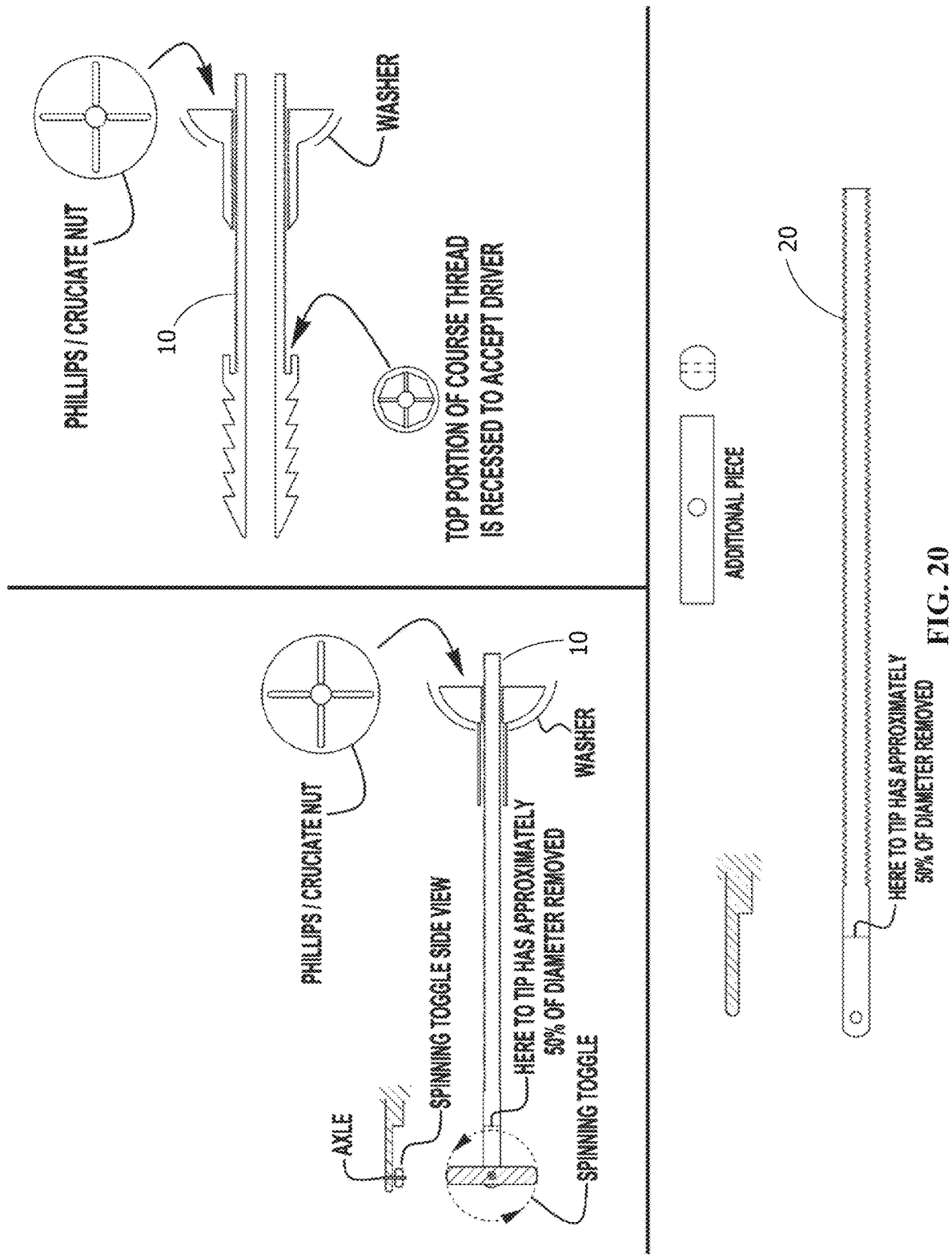

In alternate embodiments, the collet 50 may extend distally to form a sleeve that extends along at least a portion of a coupling component 20 that is inserted there through wherein the length of the frustoconical portion is greater than in the embodiments shown in the aforementioned drawings. Referring to the drawings, FIGS. 19 and 20 depict some such embodiments. Of course, in yet other embodiments, the distal end of the collet 50 may extend along substantially all of the length of the coupling component 20. In some such embodiments, a further locking component (not shown) may be provided which attaches to the distal end of the coupling component 20 and extends proximally to receive and engage the distal end of the elongated collet 50. In some such embodiments, the extended sleeve closely contacts the surface of the coupling component 20 providing enhanced locking engagement therewith. According to such specific embodiments, the extended sleeve may be adapted with a taper to allow insertion into the proximal surface of the bone to further enhance fixation and securement to the bone. Optionally, the distal sleeve 90' may have on its exterior surface features or texture that further enhance engagement with bone, particularly when the taper is inserted therein.

Referring again to FIG. 6, the securement ring 55 is sized to rest in the circumferential recess 53 of the collet 50. The securement ring 55 may be made of a minimally flexible material and used to act as the primary circumferential retaining force to secure the collet 50 and its slidable engagement with the coupling component 20, used without the locking cap 60. The securement ring 55 resides within the circumferential recess 53 of the collet 50 for both the open and closed configurations of the locking assembly 40, sliding from a proximal open (provisionally locked) position, and allowing movement along the axis to a distal closed/locked configuration, whereby the circumferential diameter compresses the securement ring 55 and the collet 50 into a locked state in compressive communication with the coupling component 20. According to the disclosure herein, the securement ring 55 is formed with a material that is non-elastic to minimally elastic and slipped over the proximal end of the collet 50 prior to assembly on the coupling component 20 and will retain close engagement and assembly of collet 50 embodiments that comprise two or more parts in a partially or provisionally closed configuration.

In some examples, the securement ring 55 is formed of silicone. In alternate examples, other suitable materials may be used to provide the needed elasticity and stiffness. In the various embodiments, the material, such as silicone, will be compressed by the inference of the locking cap 60 with the securement ring 55 in the open configuration to maintain the securement of the locking cap 60, and will remain sufficiently flexible to prevent compression and closure of the collet 50. Further, the material will be more fully compressed when in the closed position, thereby exerting compressive force on the collet 50 to lock and close it. Thus, the material is capable of expanding in various directions when under compressive force, and can act as a spring closure to secure but not lock the collet 50 except when the fully closed compressive force of the locking cap 60 is applied. Of course it will be appreciated that other materials having the desired properties may be selected and that alternative materials may be selected from flexible and shape memory metals, such as nitinol, the selection of material being non limiting.

In yet other embodiments, the securement ring 55 may be formed of a more rigid material, such as, for example, polymers and metals as described further herein below, and according to such embodiments, the securement ring 55 may be segmented, or wound like a spring, or it may comprise a plurality of circumferentially arranged slits that confer flexibility and spring like qualities. And in yet other embodiments, the securement ring 55 may be formed with an array of multiple securement rings 55 stacked and arranged in the recess of the collet 50 formed of the same or different materials as described herein above. And in yet other embodiments, the securement ring 55 may be formed of a fabric band or a stacked array of bands. It will be understood that combinations of the afore described embodiments may be employed to provide a securement ring 55.

And in further embodiments, the securement ring 55 may be formed of a contractile material that is responsive to application of an activator such as heat, electrical, chemical or other force or means such that in a pre activated form, the securement ring 55 may be more pliable and or may have a circumferential dimension that is greater than the receiving recess of the collet 50, and in the activated form the securement ring 55 is contracted so that it becomes more rigid and or contracts to assume a smaller circumferential diameter such that it fits within and compresses against the collet 50. According to some such embodiments, the contractile securement ring 55 when activated does not operate to fully compress the collet 50, and locking of the assembly requires application of the locking cap 60. According to other such embodiments, the securement ring 55 functions as both a provisional and a fix locking component wherein the application of activation of the contractile securement ring 55 converts it from the provisional locking (open) configuration to the locked (closed) configuration, without application of the locking cap 60. Thus, according to such embodiments, the locking components are fully movable along the length of the coupling component 20. Engagement of the securement ring 55 around the collet 50 provides sufficient force to maintain the collet 50 in a slightly compressed state thereby allowing free movement of the provisionally engaged locking assembly 40 proximally and distally along the length of the coupling component 20. The securement ring 55, residing in a circumferential recess 53 on the collet 50, and fashioned out of contractile material which may be activated by heat, electrical, chemical or other means, can be activated to apply a circumferential force to the collet 50 whereby it compresses the securement ring 55 against the collet 50 to lock the assembly to the coupling component 20.

Figure 8:
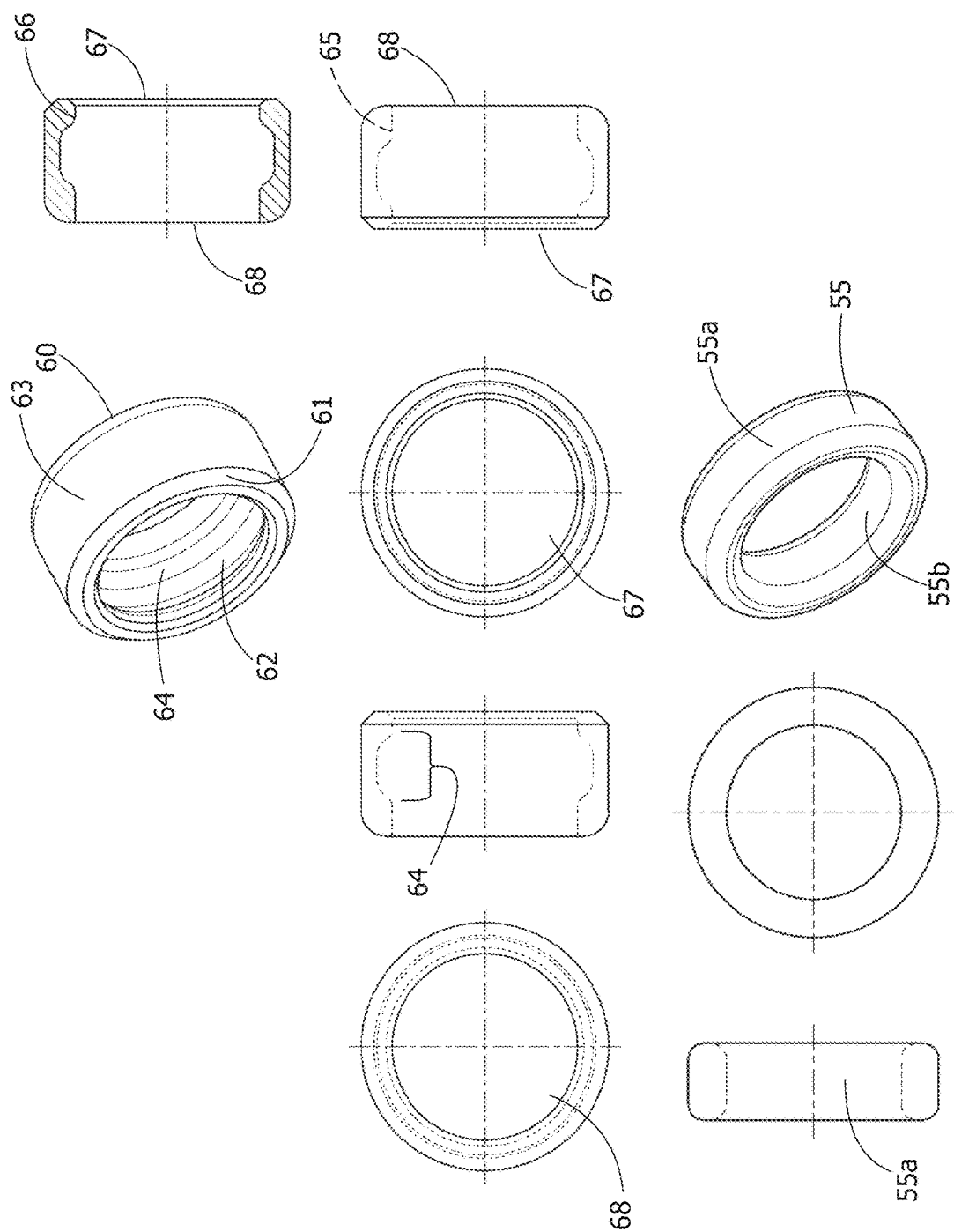
FIG. 8 shows in the top panel alternate cross sectional side and perspective views of a locking cap, and in the middle panel, alternate top, side, bottom and side views of a locking cap, and in the bottom panel, alternate side, top/bottom, and perspective views of a securement ring of the locking assembly.

In various embodiments, the securement ring 55 may be smooth with rounded edges as depicted in the figures. In yet other embodiments, the securement ring 55 may be squared at its edges, or may have combinations of square and rounded edges. Further, in alternate embodiments one or both of the internal and outer faces of a securement ring 55 may have features or textures that enhance engagement with smooth or corresponding features and textures on the outer face of the collet 50 and on the inner face of the locking cap 60. Thus, in alternate embodiments, all or a portion of the interior surface 55*b* and/or the exterior surface of the securement ring 55 may be textured with surface treatment or other features such as ridges, grooves, keels, fins, thread, dimples to enhance engagement with and locking between the securement ring 55 and either or both the collet 50 and the locking cap 60. FIG. 8 lower panel shows alternate views of a securement ring 55 according to the embodiment of the locking assembly 40 shown in FIG. 6. In various embodiments, the securement ring 55 performs the functions of maintaining provisional closure of the collet 50 in the open configuration (including also maintaining the contact and assembly of multi part collet 50), retention of the locking cap 60 while the assembly is in the open configuration, and providing compression on the collet 50 and securing the locking cap 60 in the closed configuration Referring again to FIG. 6 and FIG. 8, the locking cap 60, as depicted, has a cylindrical body 61 with cylindrical interior 62 and exterior 63 surfaces, and comprising a circumferential recess 64 on its inner surface defined by ridges 65, 66 on the distal 68 and proximal 67 interior surfaces. Referring now to FIG. 8 upper and middle panels, alternate views of the locking cap 60 are shown. As can be seen in the upper left panel, which is a cross sectional view of the locking cap 60, the proximal interior ridge 66 is slightly more prominent than the distal interior ridge 65, to facilitate ease of passage of the distal end 68 of the locking cap 60 over the securement ring 55. As can be seen in the first and third lower panels, which depict the proximal 67 and distal 68 ends, respectively, the locking cap 60 has a inner diameter that is greater at the distal end 68 vs. the proximal end 67 to further ensure that the locking cap 60 can pass over the securement ring 55 and not pass beyond the securement ring 55 distally. In various embodiments, the locking cap 60 may be smooth with rounded edges as depicted in the figures. In yet other embodiments, the locking cap 60 may be squared at its outer edges, or may have combinations of square and rounded edges. Further, in alternate embodiments one or both of the internal and outer faces 63, 62 of a locking cap 60 may have features or textures that enhance engagement with smooth or corresponding features and textures on the outer face of the securement ring 55. Further, it will be appreciated by one of skill in the art that the locking cap 60 may be formed as a securement ring 55 or as a unitary closed locking cap 60 that is engageable with a collet 50 and securement ring 55 subassembly, thus, the term used herein to refer to the locking cap 60 is not intended to be limiting. In alternate embodiments, all or a portion of the interior and/or the exterior surface 63, 62 of the locking cap may be textured with surface treatment or other features such as ridges, grooves, keels, fins, thread, dimples to enhance engagement with and locking between the locking cap 60 and the securement ring 55.

Example 2: Clinical Technique

In alternate embodiments, one or more adaptations to the locking assembly 40 and its components are contemplated to enable ready use with other stabilization implants, such as, for example, stabilization plates, such as bone plates. In accordance with one such embodiment, the locking assembly 40 is adapted to be engaged within a through hole or seat in a stabilization implant, formed from a metal or other suitable implant material. In various embodiments, the stabilization implant comprises one or more locking assembly 40 receiver portions 24 that are shaped and comprise engagement features, such as threads, for achieving locking engagement with a locking assembly 40. In an exemplary embodiment, the seat in the stabilization implant is concave hemispherical and the outer base of the collet seat 55' is correspondingly convex hemispherical, and each are threaded for engagement. In another exemplary embodiment, the seat in the stabilization implant is a cylindrical through hole and the collet seat 55' is cylindrically shaped at least at a portion including or distal to its proximal end and at its distal end, and each is threaded for engagement.

One of ordinary skill will appreciate that the corresponding shapes and engagement features may vary. Moreover, it will also be appreciated that a stabilization implant may comprise one or more types of engagement features for locking assemblies 40 according to the instant invention, as well as for fasteners known in the art such as conventional screws. Further, it will be appreciated that stabilization implants may be provided preassembled with one or more locking assemblies 40 according to the instant invention.

In use by an operator, installation of the components of the exemplary compression fixation system 10 for element fixation, including bone element fixation as described above, includes initial selection of a coupling component 20 device that is to be inserted through the elements to be fixed. An anchor component of the coupling component 20 is then actuated to engage with the element that is most distant from the operator, and a locking assembly 40 is slid over the coupling component 20 in a coaxial orientation towards the two or more elements and pressed against the element most proximal to the operator while at the same time the coupling component 20 is held under tension until the desired compression is achieved. The locking assembly 40 is then actuated into a locked configuration relative to the coupling component 20 and the elements, to thereby fix the assembly and maintain the desired compression.

When the elements being compressed are bone, then, consistent with suitable clinical practice, the system is retained intact so that compression is maintained over the clinically appropriate healing period. In some embodiments, the compression fixation system 10 is adjusted during the healing to maintain, increase, or reduce compression. Optionally, the system may be removed from the bone after healing.

Of course, it will be appreciated that the locking assembly 40 may be used with other coupling components 20 that lack an anchor and comprise other features that are not described herein. Indeed, in some embodiments, the locking assembly 40 may be adapted and scaled to engage with coupling components 20 that are substantially smaller than bone pins and wires, and with coupling components 20 that are substantially larger scale. Accordingly, the references to "proximal" and "distal" in regards to the exemplary coupling components 20 described herein are not intended to be limiting, and generically, the orientation of the locking assembly 40 as used herein and as may be used in other applications is not in any way limiting.

Example 3: Instruments for Engaging and Tensioning System Components

The compression fixation system 10 also includes instruments for assembling and locking the coupling component 20 and locking assembly 40 components.

Figure 9:
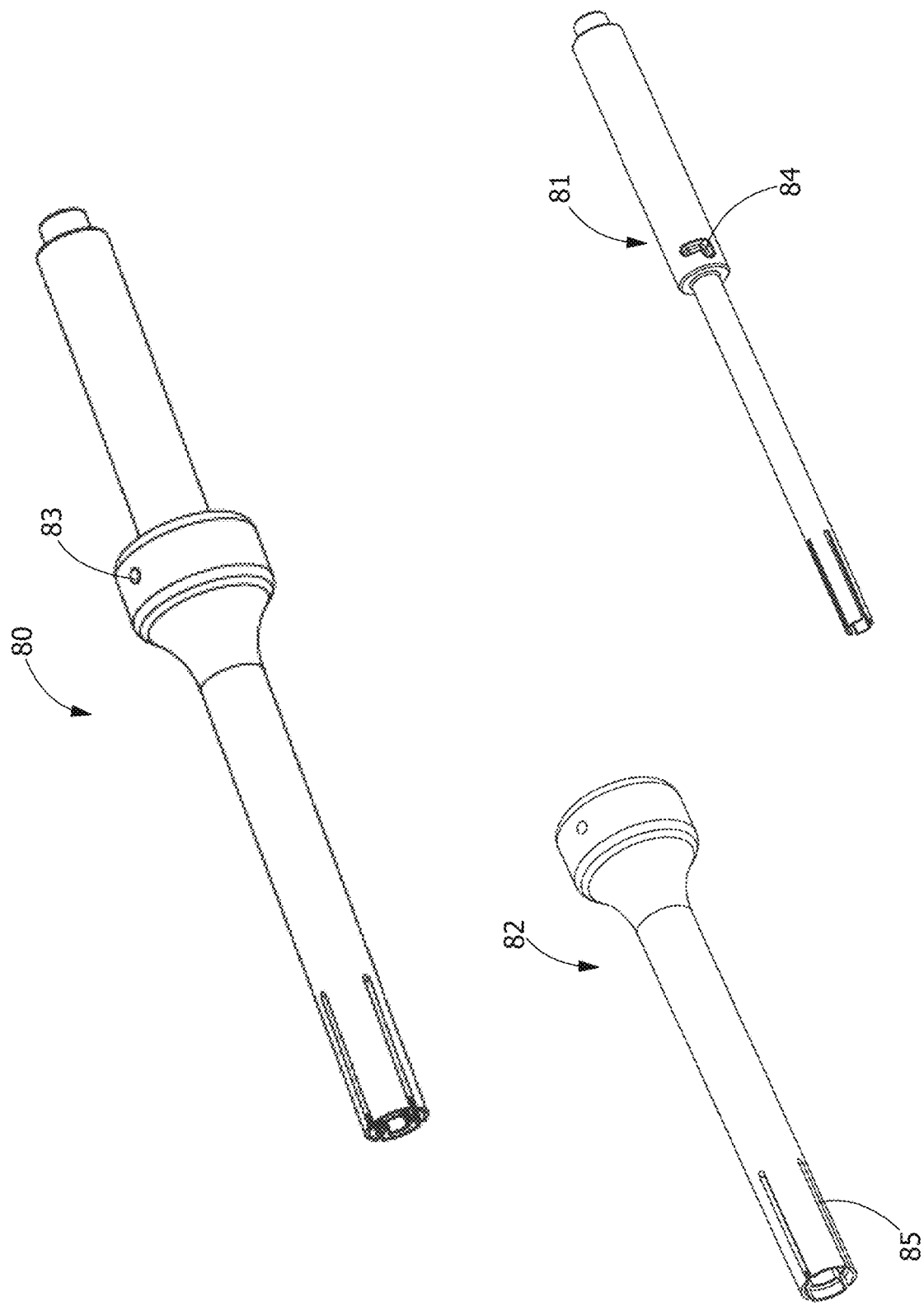
FIG. 9 shows in the upper panel, a perspective view of an embodiment of assembled insertion tools, and in the lower left and right panels, respectively, perspective views of the disassembled outer and inner sleeve components of the insertion tools.
Figure 10:
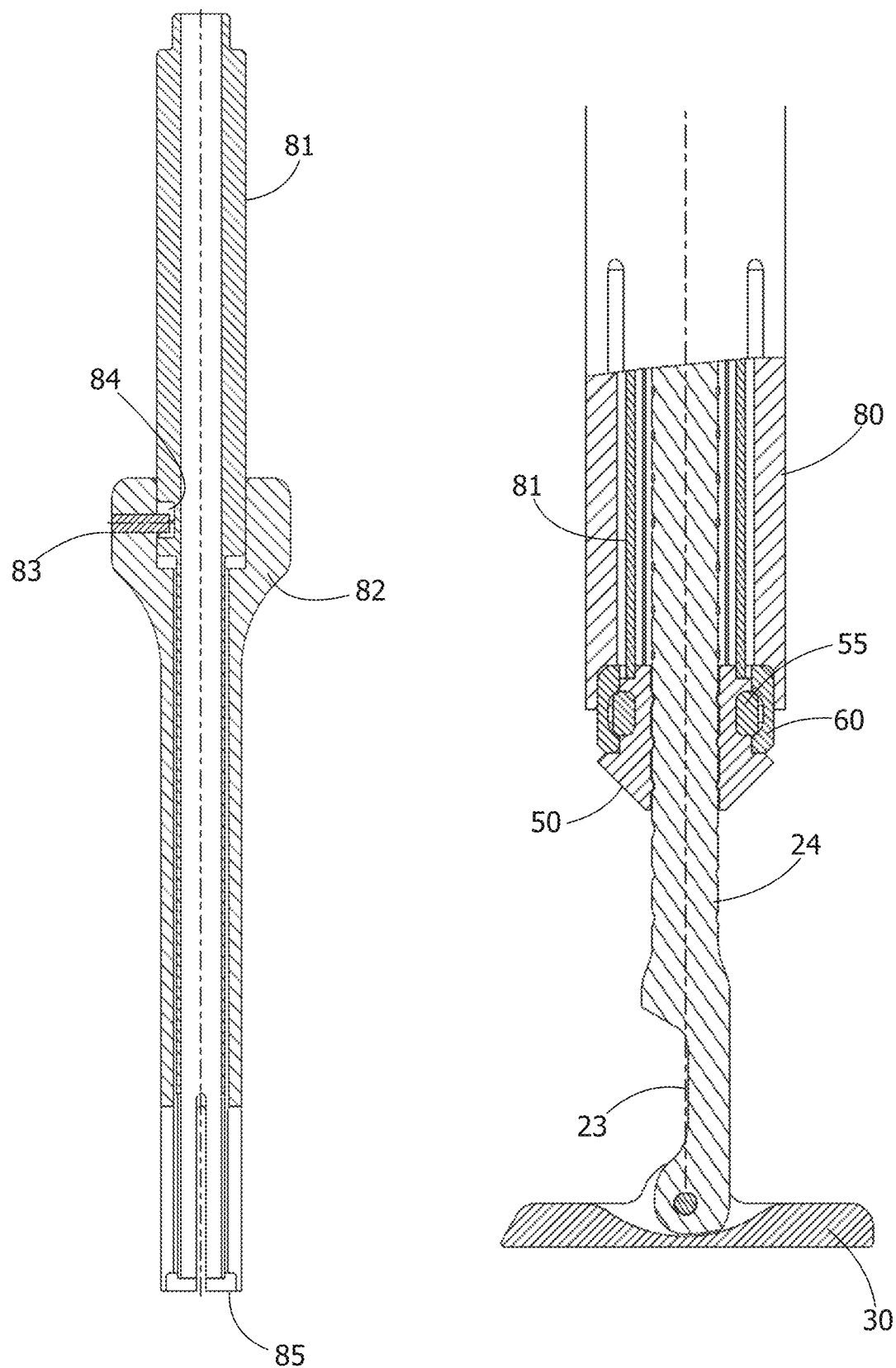
FIG. 10 shows in the left panel a cross sectional perspective view of the assembled insertion tools, and in the right panel, an cross sectional side view of the embodiment of a fully assembled compression fixation system engaged with coupling component locking assembly.
Figure 11:
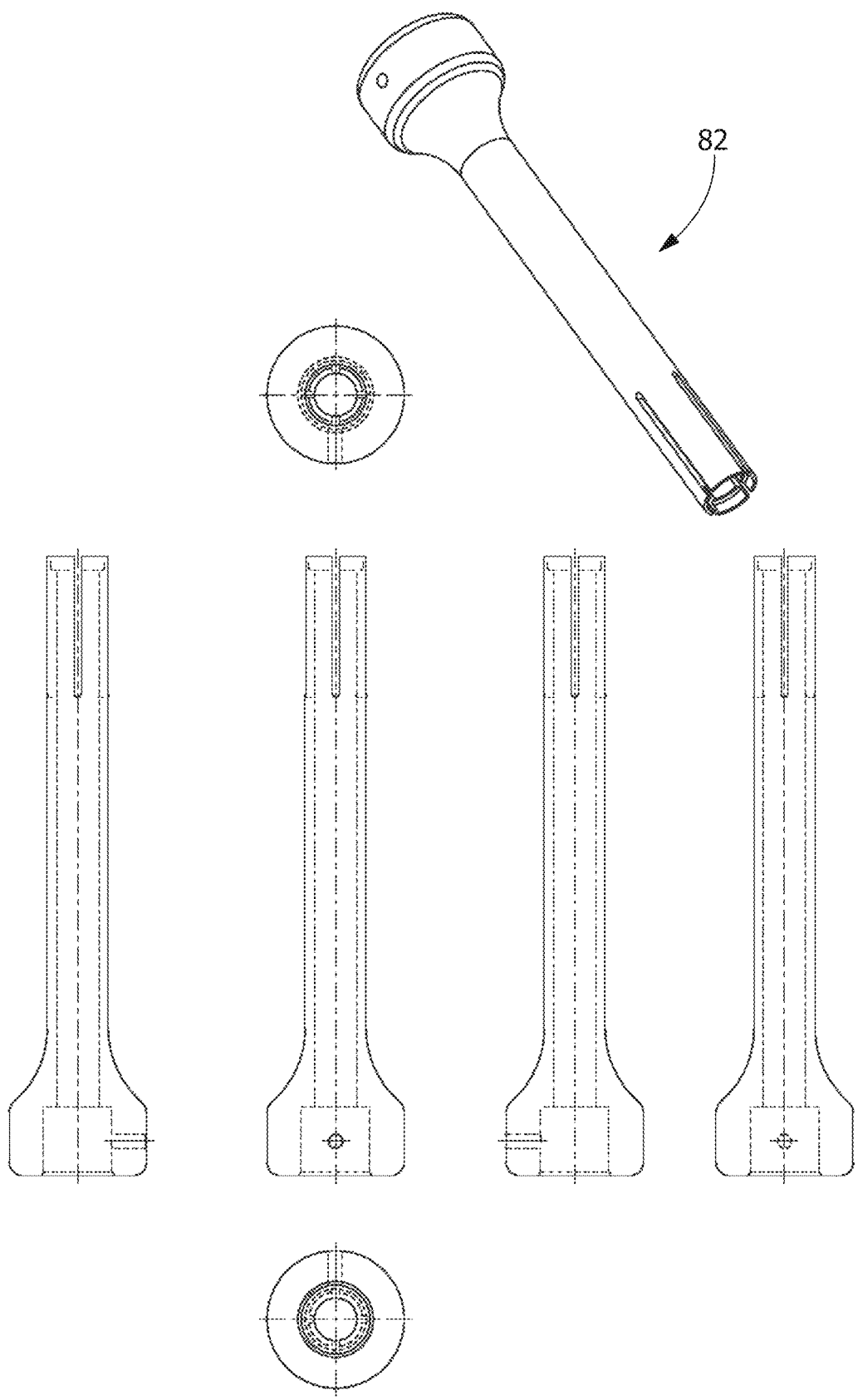
FIG. 11 shows alternate top, side, front, side, back, bottom and perspective views of the outer sleeve of the insertion instrument shown in FIG. 9.
Figure 12:
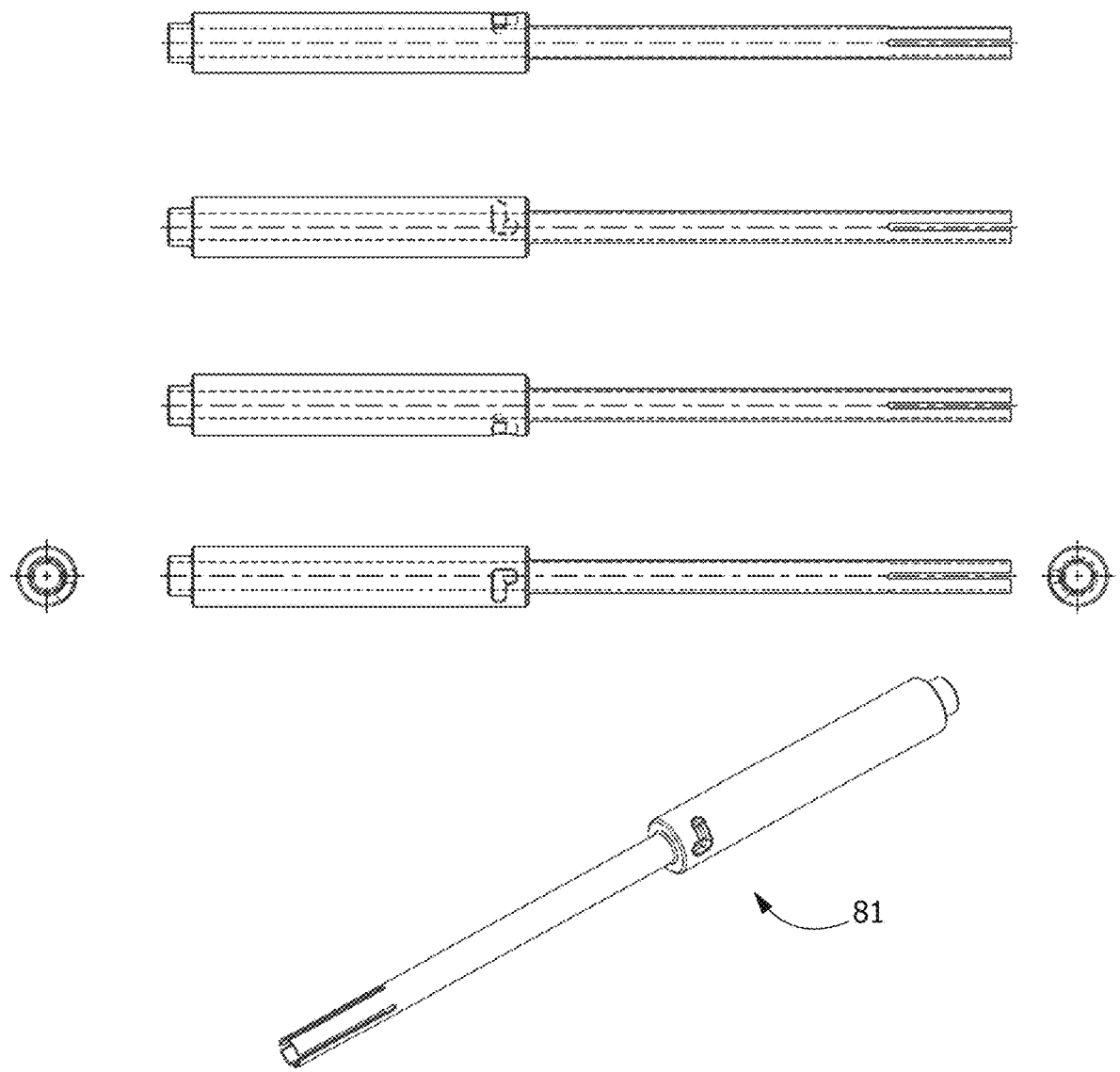
FIG. 12 shows alternate top, perspective front, side, back, side and bottom views of the inner sleeve of the insertion instrument shown in FIG. 9.
Figure 13:
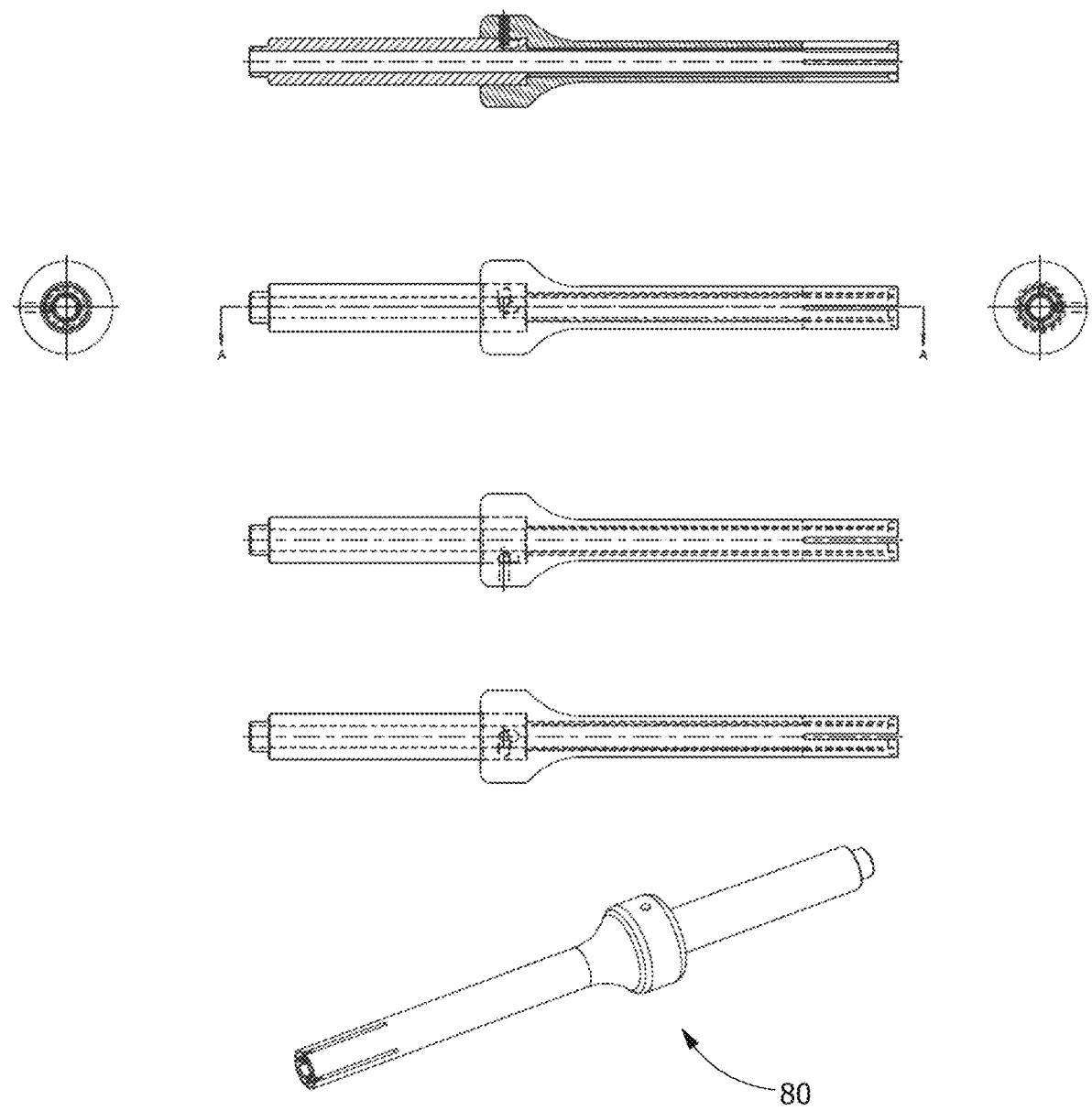
FIG. 13 shows alternate top, perspective front, side, back, cross sectional side, and bottom views of the inner sleeve of the insertion instrument shown in FIG. 9.

One exemplary instrument includes a locking assembly 40 insertion tool 80, shown in perspective view in FIG. 9. The insertion tool 80 operates to maintain orientation and alignment of the locking assembly 40 components and the coupling component 20 and can be actuated to reduce and lock the locking assembly 40 components, or loosen and unlock the locking assembly 40 for adjustment during healing or post treatment removal of the system. Referring again to the drawings, FIG. 9-FIG. 13 show alternate views of the components of an exemplary embodiment of a locking assembly 40 insertion tool 80 for achieving placement, component reduction, friction tensioning, locking and unlocking of a locking assembly 40 as described herein. Referring now to FIG. 9, the insertion tool 80 includes two nesting elongate sleeves 81, 82, each having a substantially cylindrical interior, the inner sleeve 81 having an internal and external cylindrical shape and dimensioned to closely interfit with the cylindrical interior 62 of the outer sleeve 82. As depicted in FIG. 10, which is a cross sectional view of the interfitted sleeves 81, 82, the insertion tool 80 includes at least one pin 83 that may be press fit into the outer sleeve 82. The pin 83 can be actuated to engage with and constrain the outer sleeve 82 to the inner sleeve 81 engagement in a slot 84 in the body of the inner sleeve 81. Upon engagement of the at least one pin 83, the outer sleeve 82 is able to freely rotate along the distance of the slot 84 about the inner sleeve 81. The outer sleeve 82 can also translate axially relative to the inner sleeve 81, but only a short distance defined but the proximal and distal boundaries of the pin 83 engagement slot. This distance corresponds roughly to the amount of translation needed to engage the locking cap 60 to the collet 50. FIG. 11-13 each show in various views each of the outer sleeve 82, the inner sleeve 81, and the assembled insertion tool 80 components.

Referring again to FIG. 10, each of the sleeves 81, 82 of the depicted locking assembly 40 insertion tool 80 inter-engages with at least a portion of the external surface of one or more of the collet 50 and the locking cap 60. The outer sleeve 82 is adapted with an interior groove 85 feature that inter-engages with the outer proximal edge of the locking cap 60 to stabilize it relative to the other components of the locking assembly 40. The inner sleeve 81 is adapted to inter engage with the proximal frustoconical end of the collet 50. The engagement there between enables differential securement of the insertion tool 80 to the collet 50 to enable downward pressure on the collet 50 for engagement of the collet 50 with the bone without actuating downward pressure on the locking cap 60. As further described herein, use of the tensioning tool first reduces the bone and the locking component into engagement with the bone. Thereafter, engagement of the inserter pin 83 enables discrete actuation of the outer sleeve 82 to compress the locking cap 60 against the collet 50 and securement ring 55 to snugly lock the locking assembly 40 in tight engagement with the coupling component 20.

Should removal and adjustment of the locking assembly 40 be required, a flat driver or other instrument can be inserted between the distal end of the locking cap 60 and the distal edge of the securement ring 55 recess 64 to disengage the locking cap 60 from the securement ring 55. In some embodiments, such as shown in FIG. 10, the distal edge of the locking cap 60 and the opposing distal edge of the recess in the collet 50 may be chamfered to facilitate insertion of a tool for disengagement. Of course, other instruments may be used to disengage the locking cap 60 and the collet 50, such as a circumferential grip that can grasp and pull the components apart. FIG. 10 right panel shows a cross sectional view of the insertion instrument inner and outer sleeves engaged with the compression fixation system 10. As can be seen, the inner sleeve of the insertion tool 80' is engaged with features of the proximal end of the collet 50, and the edges of the outer sleeve are engaged with the outer edges of the locking cap 60.

Figure 14:
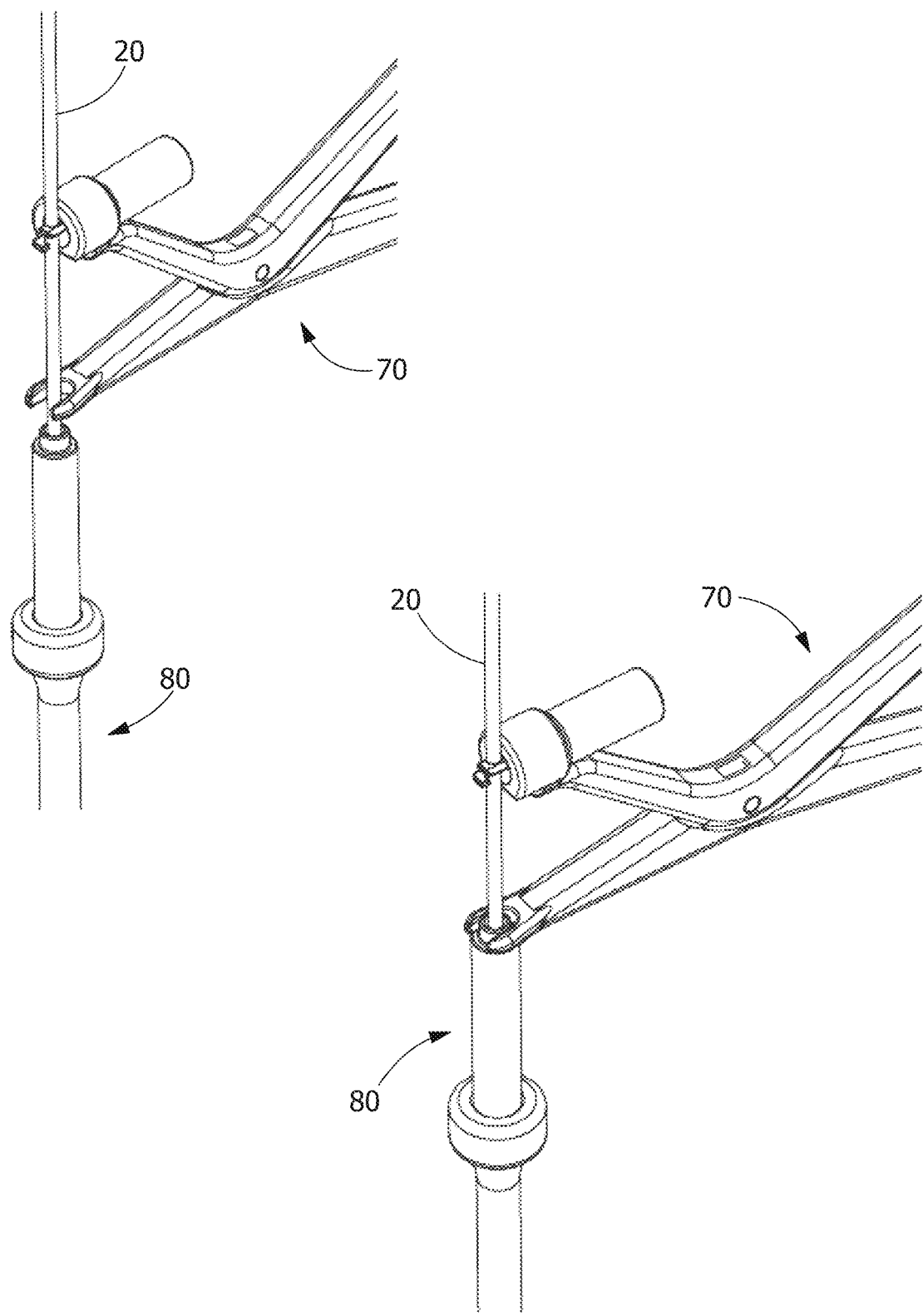
FIG. 14 shows enlarged alternate perspective views of the assembly shown in FIG. 1, the left panel showing the engagement of the tensioning instrument with the coupling component pre-tensioned, and the right panel showing the same assembly after an actuation of the tensioning instrument.
Figure 16:
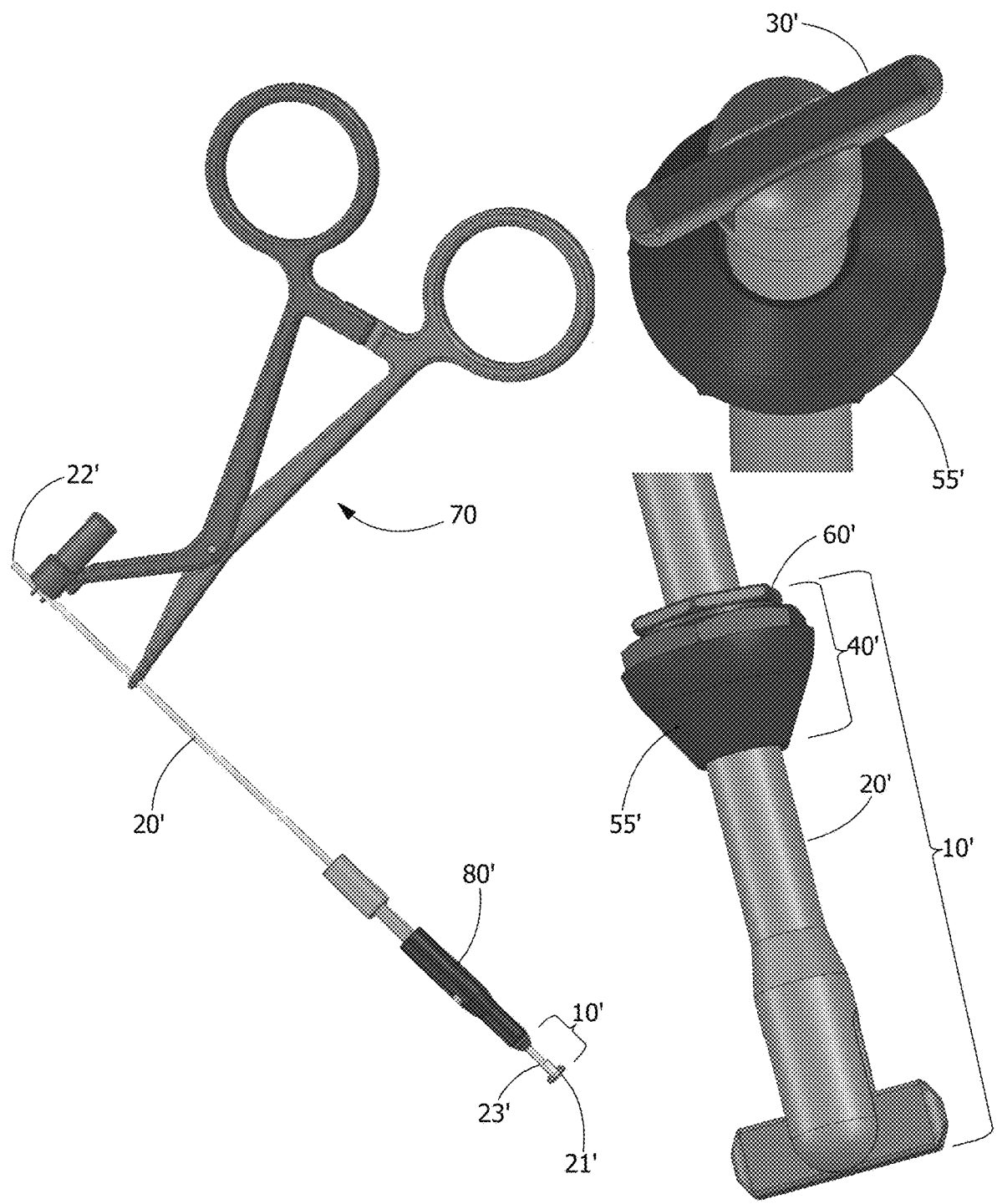
FIG. 16 shows in the upper panel a side view of a second embodiment of a fully assembled compression fixation system engaged with coupling component tensioning and insertion tools, and in the lower left panel a side view of the locking assembly and coupling components, and in the lower right panel a bottom perspective view of the locking assembly and coupling components.

Another exemplary instrument includes a tensioning instrument 70 that clamps the coupling component 20 to stabilize it and enable maintenance of tension during locking assembly 40 securement. The tensioning instrument is shown in FIG. 1 and FIG. 16, for example, and in various views in FIG. 14 and FIG. 16. Referring to FIG. 1, the exemplary embodiment of the tensioning instrument 70 is shown engaged at its proximal end with the proximal end of the coupling component 20 and is engaged at its distal end at a more distal locus on the coupling component 20 near the proximal end of the insertion tool 80. Referring now to FIG. 14, upper right panel, the exemplary embodiment of the tensioning instrument comprises a handle portion 71 that actuates opposing gripping elements 72 around a pivot axis, whereby actuation of the handle 71 moves the opposing elements 72 towards and away from one another.

Figure 15:
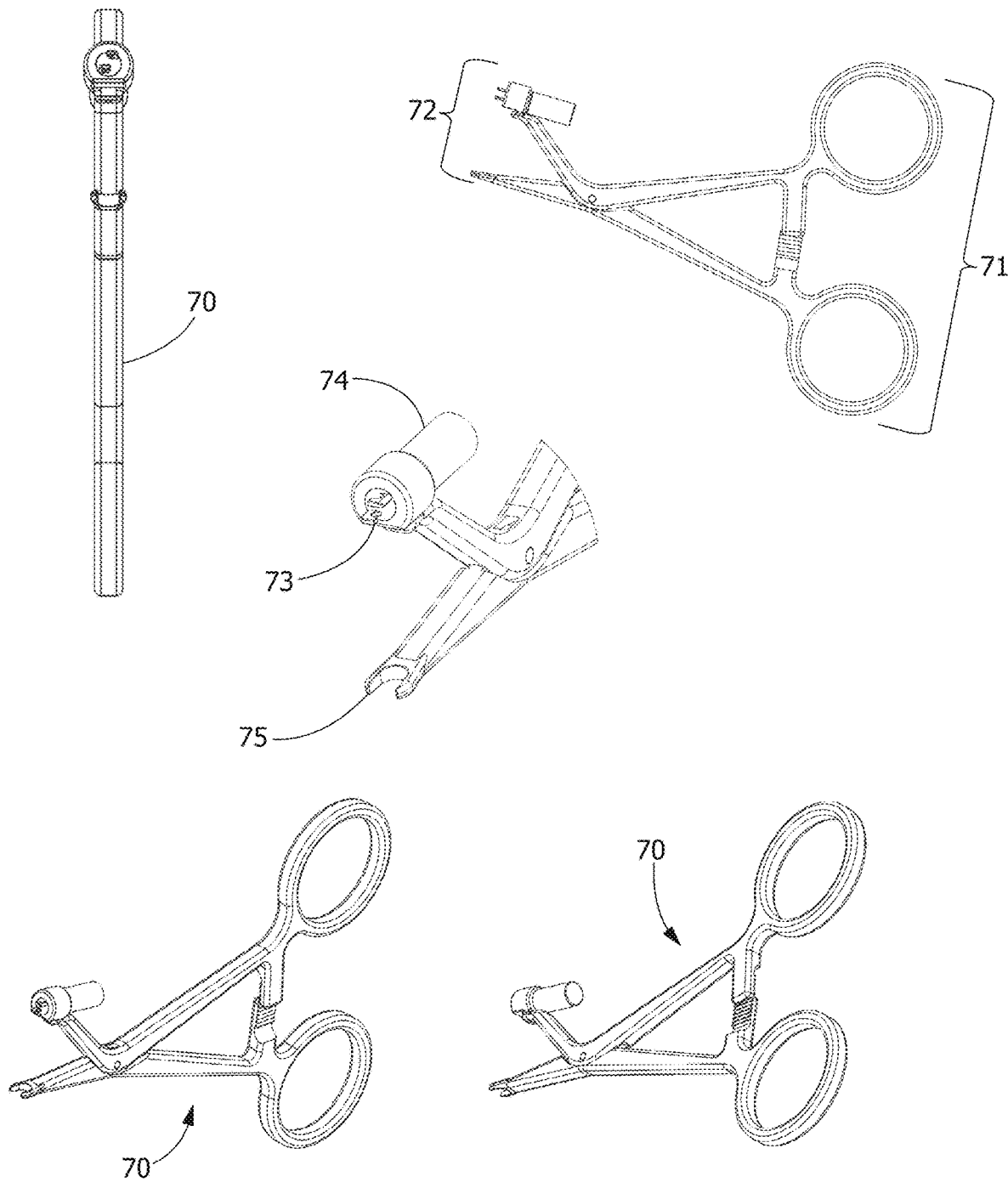
FIG. 15 shows alternate views of a tensioning instrument, the upper left panel showing a top view of the instrument, the upper right panel showing a side view, the middle panel showing a close up view of the coupling component engagement features, the lower left and right panels showing respective front end and back end perspective views of the tensioning instrument.

Referring now to FIG. 15, close up detail in the center panel shows the tensioning tool 70 comprises at its proximal grip element 73 a clamp actuation sleeve 74 with opposing clamping means extending therefrom and configured to receive the coupling component 20 in a central channel defined through the clamping means. The proximal grip element 73 of the insertion instrument locks onto the coupling component 20. The tensioning tool also comprises a distal grip element 75 that engages with and articulates to push down on the top of the insertion tool 80, which in turn presses on the top of the locking assembly 40. In use, the instrument grips 72 are affixed to a coupling component 20 as shown, for example, in the upper panel of FIG. 15, the tool handle 71 is squeezed by the operator to rotate the proximal grip element 73 away from the distal grip element 75, thereby actuating upward movement of the proximal end of the coupling component 20. This motion causes the lower grip element 75 of the tool 70 to displace downward into contact with the proximal end of the inner sleeve 81 of the insertion tool 80. Repeated squeezes of the handle 71 further actuate gripping and upward displacement of the coupling component 20, thereby driving the inner sleeve 81 of the insertion tool 80 assembly and locking assembly 40 distally, and forcing the distal end of the collet 50 against the proximal bone. The effect of actuation of the insertion instrument 80 is to reduce the two or more bone elements (i.e., compress them against one another effectively reducing the space there between) and at the same time reduce the clearance between the distal end of the locking assembly 40 and the proximal bone. Tensioning is complete when the collet 50 at the distal end of the locking assembly 40 is firmly pressed against the bone. The tensioning tool 70 handle 71 is locked to maintain tension on the coupling component 20 while the locking assembly 40 is engaged and secured. Engagement of at least one side pin 83 of the insertion instrument enables securement of the inner sleeve to the outer sleeve of the insertion instrument, and downward compression on the insertion instrument drives engagement and final closure of the locking assembly 40.

It will be appreciated that the instruments described herein are merely representative, and that more or fewer instruments comprising the same features may be provided. Thus, in some embodiments, the features of one or more of the tensioner, insertion tool, and reducer may be integrated into a single instrument. Alternately, in other embodiments, the components of the instruments may be modular, such that, for example, the sleeves of the insertion tool may be sequentially assembled, or they may be provided in combination with the locking assembly such that the operate need only slip the locking assembly/insertion and reducer assembly on to the coupling component without the need to assemble them in series.

The instruments, and the coupling component and one or more components of the locking assembly may be formed out of any suitable biocompatible material and combinations thereof, including those used conventionally in the art. Such materials include but are not limited to: metals such as, for example, stainless steel (such as 316 LVM, per ASTM F1350, electropolished and passivated), titanium alloys (such as TI-6AL-4V, per ASTM F136), cobalt alloys, superelastic metals, such as nitinol; polymers, such as polyester and polyethylene, polyether ether ketone (PEEK); and resorbable synthetic materials such as, for example, suture material and polylactic acid.

Example 4: Threaded Torsional Locking Compression Fixation System

Figure 17:
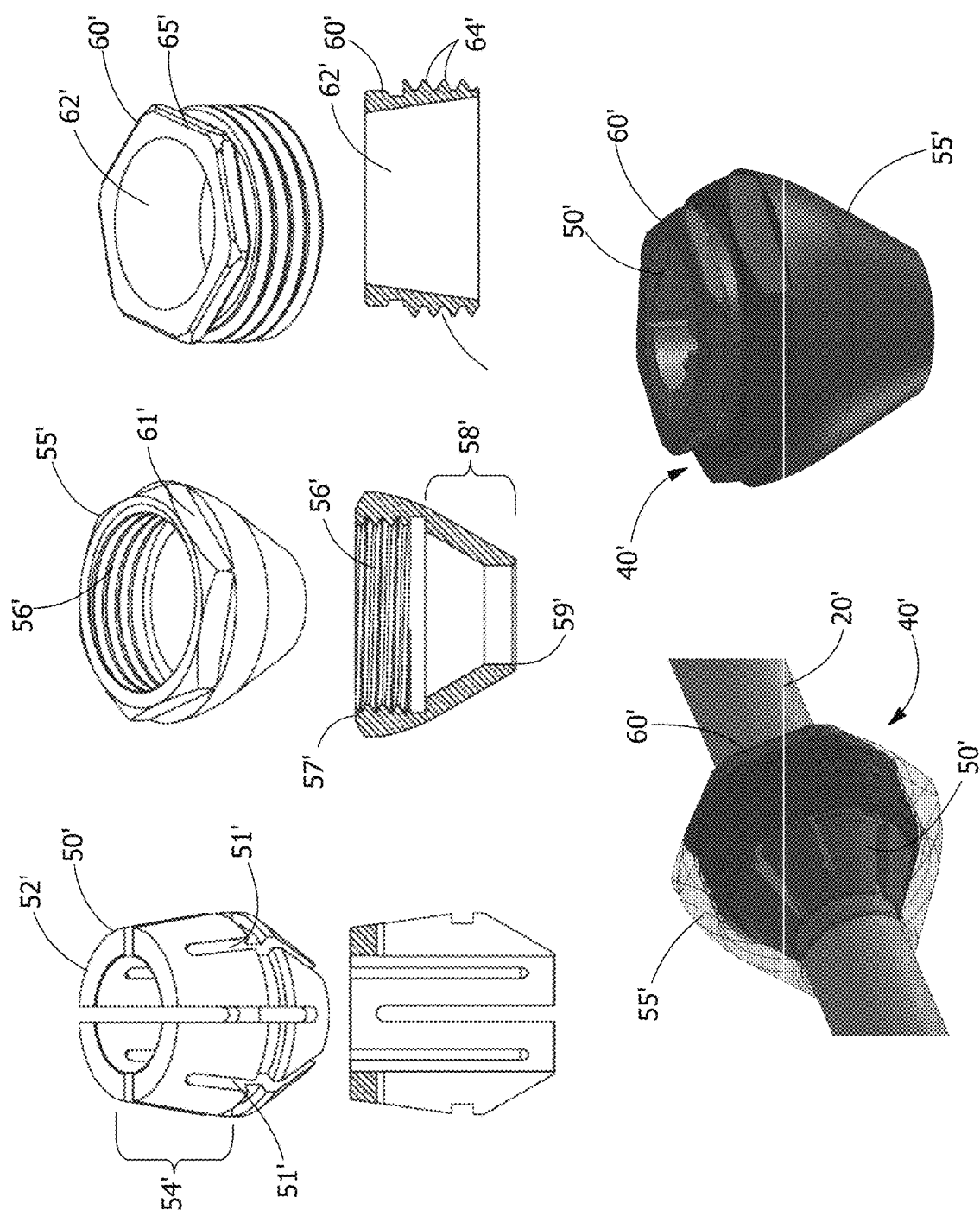
FIG. 17 shows various views of components of an alternate exemplary embodiment of a locking assembly, including in the upper and middle panels, respectively, solid and cross sectional views of a collet (left), a collet seat (center), and a compression nut (right), and in the lower left panel the exemplary locking assembly assembled with the coupling component inserted through the central bore, and in the right panel the assembled locking assembly components form a channel there through for receiving a coupling component to achieve locking fixation with the coupling component.
Figure 18:
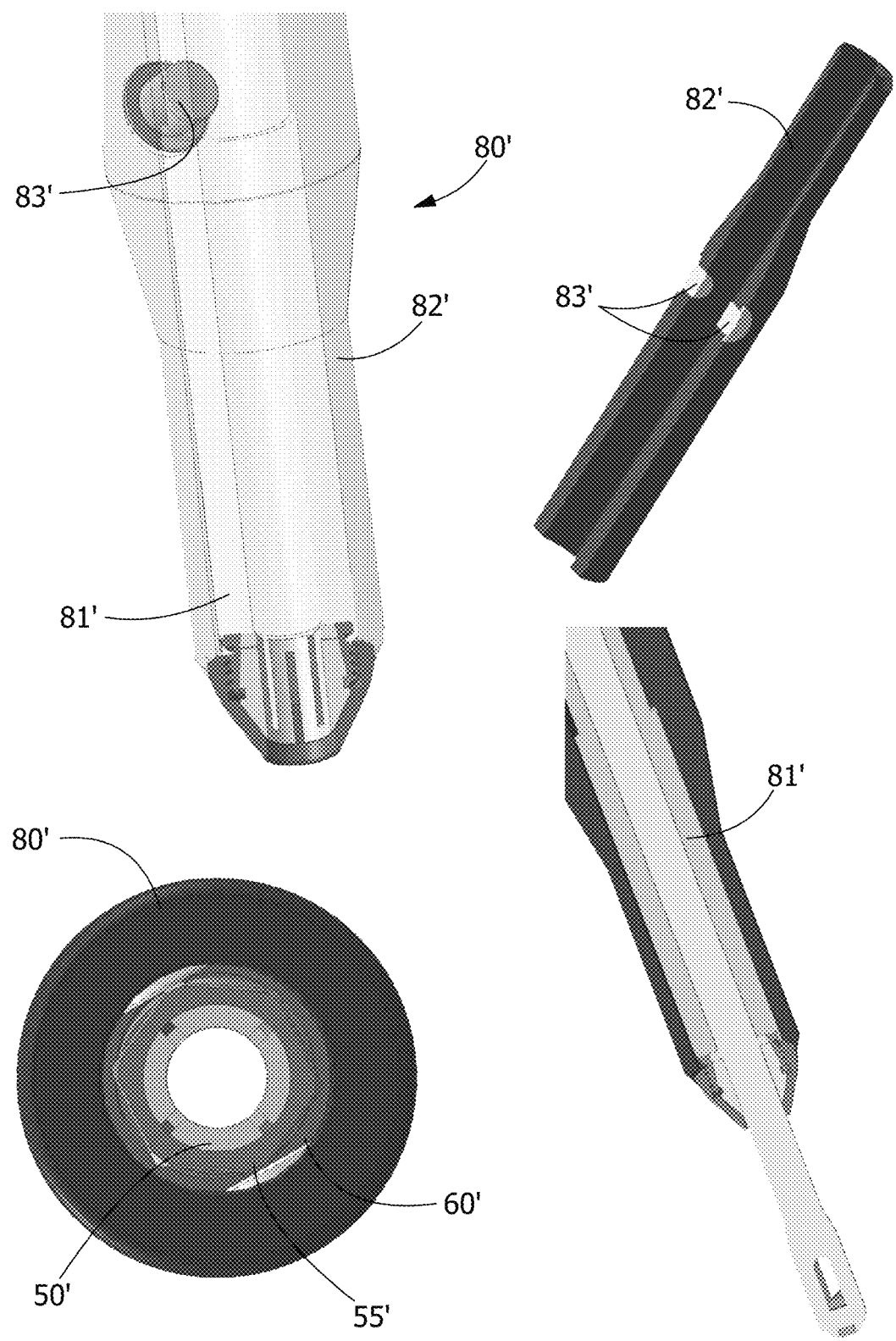
FIG. 18 shows in the upper left panel an end view of the counter torque insertion tool engaged with an assembled locking assembly, showing the edges of the opposing pins, and in the upper right and lower left panels alternate cross sectional views of the assembly, and in the lower right panel a cutaway view of the outer sleeve of the counter torque insertion tool showing in a depicted embodiment opposing pins that are press fit into the outer sleeve.

Referring now to FIG. 16-FIG. 18, various views of an alternate embodiment of a compression fixation system 10' are shown. FIG. 16 shows a side view of a fully assembled compression fixation system 10' engaged with coupling component 20' tensioning and locking assembly 40' inserter instruments.

The compression fixation system 10' includes a coupling component 20' that is selected from suitable wire and other bone pins and similar rod type devices, such as, for example K-wire. The coupling component 20' is adapted at a distal first end 21', intended to be most distal to the operator, with an anchor portion 23' for fixation within or on a distal outer surface of a first bone element. The coupling component 20' is further adapted at a proximal second end 22', intended to be most proximal to the operator, with a locking assembly 40' receiver portion 24' that is generally rectilinear. In various embodiments, at least the proximal second end 22' portion of the coupling component 20' is substantially rectilinear, and cylindrical, while the distal and a medial portion of the coupling component 20' may be other than rectilinear or may be initially rectilinear and manipulated by the operator for optimal engagement and shape conformity with the two or more elements to be fixed.

The distal anchor portion 23' of the coupling component 20' may be selected from any of a number of anchors known in the art, and generally selected from (i) those that are adapted to engage with and remain substantially within and anchor to a bone, and (ii) those that extend through bone and are adapted to engage with an outer surface of a bone or bone fragment, or a plate or other non-bone material that is intended to be held adjacent to the distal bone element. Some examples of anchors that are adapted to engage with and remain substantially within and anchor to a bone include self or non-self tapping threads, and bone engagement features that can engage by press fitting such as keels, ribs and fins. Some examples anchors that extend through bone and are adapted to engage with an outer surface include coils, barbs, and toggles.

Referring again to the drawings, enlarged views of the distal portion of an exemplary embodiment of a coupling component 20' are shown in FIG. 16. As depicted, the anchor is a toggle anchor 30', which is pivotal around an axis that is perpendicular to a long axis of the coupling component 20'. FIG. 16 lower left panel shows a side view of the deployed toggle anchor 30', and FIG. 16 lower right panel shows a distal to proximal end perspective view of a deployed toggle anchor 30'. In an insertion configuration, the toggle anchor 30' is pivoted so that it is aligned with the long axis of the coupling component 20' to enable insertion into the bone and allow clean exit from a proximal end of the bone. Actuation of the pivot feature of the toggle anchor 30' rotates its position so that it is perpendicular to the axis of the coupling component 20', and is deployed to operate as an anchor, thereby preventing back out of the coupling component 20' from the bone. While the toggle anchor 30' as shown is engaged with the coupling component 20' in a split end configuration, one of ordinary skill will understand that the toggle anchor 30' may be attached by any one of other possible means, such as a cantilever attachment to one side of the coupling component 20', as described herein above, and as shown in other drawings, specifically FIG. 10 and FIG. 20.

One of ordinary skill will appreciate that the depicted coupling component 20' can be provided in variable lengths, with or without curves or bends, with or without surface texture and surface features. Moreover, while the depicted coupling component 20' is generally cylindrical in shape from the proximal end and terminates at the exemplary anchor, one of ordinary skill will appreciate that the shape may be other than cylindrical (i.e., the cross section may be other than circular). Thus, in some alternate embodiments, the coupling component 20' may have a cross section that is selected from one of the following non-limiting examples, including, scalloped, star shaped, hexagonal, square, and ovoid. Likewise, the coupling component 20' may be uniform in cross sectional shape and width along its entire length, or it may comprise regions that vary and include combinations of different cross sectional shapes, widths/diameters, and textures. Thus, it will be appreciated that any particular region which may be substantially rectilinear for receiving a locking assembly 40' may be cylindrical or otherwise shaped and may be smooth or have any one of a variety of surface features such as grooves or notches and textures that comprise knurling or other non-smooth texturing. Further, while the exemplary embodiment of the coupling component 20' shown in the drawings terminates as a cylinder at the proximal end, there may be alternate shapes and features at the proximal end that are suited for engagement with a tool or instrument. Thus, in some non-limiting examples, the coupling component 20' may comprise at its proximal end a hemispherical, conical or frustoconical feature, or a star, scallop or hex cross-section, or combinations of these.

In some alternate embodiments, the coupling component 20' may have a diameter that permits cannulation through at least a portion of the coupling component 20'. In some examples such embodiments would include cannulated bone wires and pins. In other such embodiments, examples include tubes, conduit, pipes, and other substantially hollow components that are suitable to receive a locking assembly 40' along at least a portion of the component that is rectilinear.

The compression fixation system 10' also comprises a locking assembly 40'. Referring again to FIG. 17 lower right panel, a side view of a representative embodiment of a locking assembly 40' is shown inserted on and arranged concentrically with the coupling component 20'.

The exemplary embodiments of the locking assembly 40', as shown in the drawings, includes inter-engaging collet 50' (left), collet seat 55' (middle), and compression nut 60' (right) components, shown, respectively, in side and cut away views in FIG. 17 upper and middle panels. Referring now to FIG. 17 upper and middle panels, each of the compression nut 60', collet 50' and collet seat 55' components cooperate along a shared axis and inter-engage to form a locking assembly 40'. As shown, the assembled locking assembly 40' components form a channel there through for receiving a coupling component 20' to achieve locking fixation with the coupling component 20'.

The collet seat 55', collet 50' and compression nut 60' components are constructed to slide over at least a distal first end 21' of the coupling component 20' while in an open configuration, can be held stably on the coupling component 20' in a friction (engaged but not locked) configuration to enable positioning relative to the elements to be fixed, and can be actuated to achieve a locked configuration. FIG. 17 lower left panel shows an exemplary locking assembly 40' assembled with the coupling component 20' inserted through the central bore. As shown, the collet seat 55' is depicted as transparent to show the relative inter-fitting between the compression nut 60', collet 50', and collet seat 55' components. The collet seat 55' and collet 50' have complimentary engagement surfaces that inter-fit and are adapted with features to enable precise locking and prevent sliding and rotation relative to the coupling component 20'. Likewise, again with reference to FIG. 17, the compression nut 60' and the collet 50' have complementary engagement surfaces that also inter-fit and are adapted to enable secondary locking to prevent sliding and rotation relative to the coupling component 20'. An advantageous aspect of this system is that the connection and compression can be achieved without introduction of rotational insertion to the system; that is, the collet seat 55' and collet 50' are designed to engage with the compression nut 60' without rotating around the shared axis with the coupling component 20', thereby diminishing the risk of material stripping into patient tissue and ensuring optimal compression and purchase of the coupling component 20' surface. In various embodiments, the compression fixation system 10' may be provided for use by an operator in a pre-assembled state, completely disassembled, or in a state of sub-assembly.

Referring again to FIG. 17, the collet seat 55', as depicted, is generally frustoconical, with a central bore that is substantially cylindrical at its most distal end, and proximal to the cylindrical portion a distal interior wall that is frustoconical in shape and adapted to receive and inter-fit with the collet 50' when the collet 50' is inserted therein. The collet seat 55' also has a substantially cylindrical and threaded proximal interior wall 56' for inter-engagement with the compression nut 60'. The interior surface of the collet seat 55', as depicted, is generally smooth at the distal seat 58' and the seat 58' is generally conical in shape. The exterior surface of the collet seat 55' is tapered and generally smooth from the proximal 57' to the distal end 59', and includes on its proximal end 59' an instrument engagement feature 61'. The collet seat 55', as depicted, includes a hex nut configuration at its proximal end for engagement with a positioning and locking instrument. It will be appreciated by those skilled in the art that other engagement features are possible and that the disclosed engagement feature is not to be limiting. In alternate embodiments, all or a portion of the exterior surface as well as the interior surface of the collet seat 55' may be textured by surface treatment or other features such as ridges, grooves, keels, fins, thread, dimples and the like to enhance engagement with and locking between the collet seat 55' and the collet 50'. Likewise, the shape of the interior distal wall 58' of the collet seat 55' may have a shape that is other than conical, for example, it may be hemispherical.

In alternate embodiments, the collet seat 55' extends distally to form a sleeve that extends along at least a portion of a coupling component 20' that is inserted there through. Referring to the drawings, FIG. 10 and FIG. 20 depict some such embodiments. Of course, in yet other embodiments, the distal end of the collet seat 55' may extend along substantially all of the length of the coupling component 20'. In some such embodiments, a further locking component (not shown) may be provided that attaches to the distal end of the coupling component 20' and extends proximally to receive and engage the distal end of the elongate sleeve end of the collet seat 55'. In yet other embodiments, the extended sleeve closely contacts the surface of the coupling component 20' providing enhanced locking engagement therewith. According to such specific embodiments, the extended sleeve may be adapted with a taper to allow insertion into the proximal fixed element. In such case where the element is bone, the tapered distal end of the collet seat 55' sleeve may be inserted into the bone to further enhance fixation and securement to the bone. Optionally, the distal sleeve may have on its exterior surface features or texture that further enhance engagement with bone, particularly when the taper is inserted therein.

Referring again to FIG. 17, the collet 50', as depicted, is generally cylindrical, having a central bore that is cylindrical and adapted to receive the coupling component 20', a tapered distal end that is generally frustoconical a tapered proximal end, and a series of slots 51' that are generally equally spaced circumferentially, and, as depicted, alternate in origination from the proximal 52' and distal ends 53'. It will be appreciated that the slots may, in alternate embodiments, be unequally spaced, there may be fewer or more slots, and they may all originate from one or the other of the proximal and distal end. As depicted, the collet 50' has a circumferential groove or channel that is distal of the midpoint of the collet 50' and defines the boundary between the tapers of the proximal 52' and distal ends 53', referred to herein as the proximal lobe and the distal lobe, respectively, of the collet 50'. The proximal lobe 54' of the collet 50' is shaped to inter-fit with the interior surface 62' of the compression nut 60'. The distal lobe of the collet 50' is shaped to inter-fit with the interior distal wall 58' of the collet seat 55'. The exterior surface of the collet 50', as depicted, is generally smooth on each of the proximal and distal lobes. In alternate embodiments, all or a portion of the exterior surface as well as the interior surface of the collet 50' may be textured surface treatment or other features such as ridges, grooves, keels, fins, thread, dimples to enhance engagement with and locking between the distal end of the collet 50' and the collet seat 55', and between the proximal end of the collet 50' and the compression nut 60'.

Advantageously, referring again to FIG. 17, the two lobed design of the collet 50' enables uniform compression along its length and enhanced compression circumferentially against the coupling component 20' inserted there through as a result of the combined compressive force of the collet seat 55' on the distal lobe of the collet 50' and the compressive force of the compression not on the proximal lobe of the collet 50'.

Referring again to FIG. 17, the compression nut 60', as depicted, has a tapered cylindrical interior 62' surface, which is complementary to the taper of the proximal lobe of the collet 50'. The compression nut 60' has a substantially cylindrical exterior 63' surface with threading 64' at the distal end for engagement with the proximal interior wall 56' of the collet seat 55', and includes on its proximal end an instrument engagement feature 65'. The compression nut 60', as depicted, includes a hex nut configuration at its proximal end for engagement with a positioning and locking instrument. It will be appreciated by those skilled in the art that other engagement features are possible and that the disclosed engagement feature is not to be limiting. Likewise, it will be appreciated that the interior surface of the compression nut 60' may have an inverted taper or no taper at all, and it may have surface texturing or other treatment or features as disclosed herein to enhance engagement with the coupling component 20'. And in alternate embodiments, all or a portion of the non-threaded exterior surface of the compression nut 60' may be textured with surface treatment or other features such as ridges, grooves, keels, fins, thread, dimples to enhance engagement with and locking between the proximal end of the compression nut 60' and a feature that is proximal thereto.

As described herein above, various instruments are provided that facilitate use of the compression fixation system 10' components. One exemplary instrument includes a tensioning grip that clamps the coupling component 20' to stabilize it and enable maintenance of tension during locking assembly 40' locking, as shown in FIG. 1 and FIG. 16.

Another exemplary instrument includes a locking assembly 40' counter torque insertion tool 80'. The counter torque insertion tool operates to maintain orientation and alignment of the locking assembly 40' components and the coupling components 20' and can be actuated to reduce and lock the locking assembly 40' components, or loosen and unlock the locking assembly 40' for adjustment during healing or post treatment removal of the system. Referring again to the drawings, FIG. 18 depicts an alternate exemplary embodiment of a locking assembly 40' tool, namely a counter torque insertion tool 80' for achieving placement, component reduction, friction tensioning, locking and unlocking of a locking assembly 40' as described herein. Referring now to FIG. 18, the counter torque insertion tool 80' includes two nesting elongate sleeves 81', 82', each having a substantially cylindrical interior, the inner sleeve 81' having an internal and external cylindrical shape and dimensioned to closely interfit with the interior cylindrical interior of the outer sleeve 82'. As depicted in FIG. 18 upper and lower right panels, cutaway views of the outer sleeve 82' show that the counter torque insertion tool 80' includes opposing pins 83' that are press fit into the outer sleeve 82'. These pins constrain the outer sleeve to the inner sleeve via the pins engaging a groove. The outer sleeve 82' is able to freely rotate about the inner sleeve. The outer sleeve can also translate to relative to the inner sleeve 81, but only a short distance. This distance corresponds roughly to the amount of translation needed to engage the compression nut 60' to the collet seat 55'. FIG. 18 upper left panel shows a distal end view of the assembly of the counter torque insertion tool 80' and the locking assembly 40', showing the edges of the opposing pins 83'.

The depicted locking assembly 40' counter torque insertion tool 80' is comprised of concentric inner and outer sleeves 81', 82', each of which sleeves 81', 82' inter-engages with at least a portion of the external surface of one or more of the collet seat 55', the collet 50' and the locking nut. Referring now to FIG. 18 lower left panel, the outer sleeve is adapted with an interior groove feature that inter-engages with the outer proximal edge of the collet seat 55' to lock it relative to the other components of the system. Likewise, the inner sleeve 81' is adapted with notches 84' to inter-engage with corresponding features on the proximal rim of the compression nut 60'. The engagement there between enables differential axial rotation of the compression nut 60' by the counter torque insertion tool 80' while the collet seat 55' is held in place, thereby driving the mating threads of the compression nut 60' and the collet seat 55' into engagement.

In use, the threads of the collet seat 55' and nut may be partially engaged to enable friction fixation of the locking assembly 40' while tensioning is applied to tighten the coupling component 20' and firmly place the locking assembly 40' against the proximal element. Upon application of further torsional force to the counter torque insertion tool 80', the threads of the compression nut 60' and collet seat 55' are fully engaged, directing circumferential force against the upper lobe of the collet 50' and forcing the lower lobe of the collet 50' firmly into the collet seat 55' thereby locking the lower lobe to achieve locked fixation of the fattener to the coupling component 20'.

It will be appreciated that the instruments described herein are merely representative, and that more or fewer instruments comprising the same features may be provided. Thus, in some embodiments, the features of one or more of the tensioner, torque reduction tool and reducer may be integrated into a single instrument. Alternately, in other embodiments, the components of the instruments may be modular, such that, for example, the sleeves 81', 82' of the insertion tool 80' may be sequentially assembled, or they may be provided in combination with the locking assembly 40' such that the operate need only slip the locking assembly 40'/torque and reducer assembly on to the coupling component 20' without the need to assemble them in series.

While various inventive aspects, concepts and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, devices and components, alternatives as to form, fit and function, and so on) may be described herein, such descriptions are not intended to be a complete or exhaustive list of available alternative embodiments, whether presently known or later developed.

Those skilled in the art may readily adopt one or more of the inventive aspects, concepts or features into additional embodiments and uses within the scope of the general inventive concepts even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated. Further, while disclosed benefits, advantages, and solutions to problems have been described with reference to specific embodiments, these are not intended to be construed as essential or necessary to the invention.

The invention claimed is:

1. A compression fastener system comprising:
 a coupling component having proximal and distal ends, a locking assembly, and an anchor component that is integral with the coupling component at the coupling component's distal end, wherein the anchor component is a toggle, the locking assembly engageable with the coupling component and comprising
at least a first compressible collet, and
at least a first collet compression component;
wherein the locking assembly, when assembled, may be provisionally locked to enable free linear movement along the coupling component.

2. A compression fastener system according to claim 1, the coupling component comprising an elongate wire, the locking assembly also comprising a second collet compression component.

3. A compression fastener system according to claim 2, the first collet compression component comprising a collet seat that receives and is engageable with the compressible collet, and the second collet compression component comprising a compression nut that is engageable with the collet seat and is actuatable between provisionally locked and locked configurations, wherein each of the compressible collet, collet seat and compression nut are generally cylindrical and when assembled share a common center axis, and wherein the collet is engageable and compressible directly with the coupling component.

4. A compression fastener system according to claim 3, wherein engagement between the components is achieved by one of press fitting and threaded engagement between the collet seat and the compression nut.

5. A compression fastener system according to claim 4, wherein the toggle is engageable with the coupling component in a cantilever pivotal arrangement, such that in one configuration, the toggle is pivoted into linear alignment with the coupling component and is nested within a recess therein, and in a second configuration, the toggle is deployed in a generally perpendicular orientation relative to the axis of the coupling component, and wherein the engagement between the locking assembly is by threaded engagement between the collet seat comprising interior threads and a threaded compression nut comprising corresponding threads for engagement with the collet seat.

6. A compression fastener system according to claim 5, wherein at least one of (i) at least a portion of an outer surface of the distal end of the coupling component and (ii) at least a portion of an inner face of the compressible collet comprises a surface feature selected from one or a combination of ridges, grooves, keels, fins, threads, dimples, knurls, and surface texturing, and wherein the surface features of the at least one of the outer surface of the coupling component and the inner face of the compressible collet cooperate with the opposing surface of the assembly when the locking assembly is in a locked configuration to enhance the compressive securement of the locked compression fixture system.

7. A compression fastener system according to claim 6, wherein each of the at least a portion of an outer surface of the distal end of the coupling component and at least a portion of an inner face of the compressible collet comprises a surface feature.

8. A compression fastener system according to claim 7, wherein the compressible collet is selected from (i) unitary slit form that comprises at least one slit selected from a through slit and a partial slit, and (ii) a multi piece form.

9. A compression fastener system according to claim 2, wherein the first collet compression component operates to retain the compressible collet, and wherein the second collet compression component operates in engagement with the first collet compression component in a first configuration to provisionally secure the locking assembly to the coupling component and in a second configuration to fixedly secure the locking assembly into compression locking with the coupling component.

10. A compression fastener system according to claim 9, the first collet compression component comprising a flexible securement ring that is engageable with the compressible collet, and the second collet compression component comprising a locking cap that is engageable with the compressible collet and the securement ring, and actuatable between provisionally locked and locked configurations, wherein each of the compressible collet, securement ring and cap are generally cylindrical, and wherein the compressible collet is engageable and compressible directly with the coupling component, and wherein when the locking assembly and the coupling component are assembled they share a common center axis, and wherein engagement between the components is achieved by press fitting.

11. A compression fastener system according to claim 10, wherein the toggle is engageable with the coupling component in a cantilever pivotal arrangement, such that in one configuration, the toggle is pivoted into linear alignment with the coupling component and is nested within a recess therein, and in a second configuration, the toggle is deployed in a generally perpendicular orientation relative to the axis of the coupling component.

12. A compression fastener system according to claim 11, wherein at least one of (i) at least a portion of an outer surface of the distal end of the coupling component and (ii) at least a portion of an inner face of the compressible collet comprises a surface feature selected from one or a combination of ridges, grooves, keels, fins, threads, dimples, knurls, and surface texturing, and wherein the surface features of the at least one of the outer surface of the coupling component and the inner face of the compressible collet cooperate with the opposing surface of the assembly when the locking assembly is in a locked configuration to enhance the compressive securement of the locked compression fixture system.

13. A compression fastener system according to claim 12, wherein each of the at least a portion of an outer surface of the distal end of the coupling component and at least a portion of an inner face of the compressible collet comprises a surface feature, and wherein the securement ring comprises silicone.

14. A compression fastener system according to claim 13, wherein the compressible collet is selected from (i) a unitary slit form that comprises at least one slit selected from a through slit and a partial slit, and (ii) a multi piece form.

15. A compression fastener system according to claim 9, wherein the locking assembly and the coupling component are preassembled in a provisionally locked configuration, the assembly further comprising an insertion tool that is engageable with the provisionally locked assembly, the insertion tool comprising nesting elongate inner and outer sleeves, the outer sleeve adapted to engage with one of the compressible collet and the first and second compression components and the inner sleeve adapted to engage with the other of the compressible collet and the first and second compression components, the inner and outer sleeves releasably engageable between free and limited degrees of freedom around and along a shared center axis, wherein when the inner and outer sleeves are not engaged, one of the sleeves is actuatable along the axis to direct translation of the assembly distally, and wherein when the inner and outer sleeves are engaged, at least one sleeve is actuatable either around or along the axis to drive fixed engagement between the first and second compression components.

16. A compression fastener system according to claim 15, the first collet compression component comprising a flexible securement ring that is engageable with the compressible collet, and the second collet compression component comprising a locking cap that is engageable with the compressible collet and the securement ring, and actuatable between provisionally locked and locked configurations, wherein each of the compressible collet, securement ring and cap are generally cylindrical, and wherein the compressible collet is engageable and compressible directly with the coupling component, and wherein when the locking assembly and the coupling component are assembled they share a common center axis, and wherein engagement between the components is achieved by press fitting, wherein the toggle is engageable with the coupling component in a cantilever pivotal arrangement, such that in one configuration, the toggle is pivoted into linear alignment with the coupling component and is nested within a recess therein, and in a second configuration, the toggle is deployed in a generally perpendicular orientation relative to the axis of the coupling component wherein at least one of (i) at least a portion of an outer surface of the distal end of the coupling component and (ii) at least a portion of an inner face of the compressible collet comprises a surface feature selected from one or a combination of ridges, grooves, keels, fins, threads, dimples, knurls, and surface texturing, and wherein the surface features of the at least one of the outer surface of the coupling component and the inner face of the compressible collet cooperate with the opposing surface of the assembly when the locking assembly is in a locked configuration to enhance the compressive securement of the locked compression fixture system, wherein each of the at least a portion of an outer surface of the distal end of the coupling component and at least a portion of an inner face of the compressible collet comprises a surface feature, and wherein the securement ring comprises silicone, wherein the compressible collet is selected from (i) unitary slit form that comprises at least one slit selected from a through slit and a partial slit, and (ii) a multi piece form, wherein the inner sleeve of the insertion tool engages with the compressible collet and the outer sleeve engages with the locking cap, and wherein upon engagement of the sleeves the outer sleeve is actuated by displacement in a distal direction to lock the locking cap to the securement ring and thereby compress and lock the compressible collet into compressive engagement with the coupling component.

17. A compression fastener system according to claim 15, the first collet compression component comprising collet seat that receives and is engageable with the compressible collet, and the second collet compression component comprising a compression nut that is engageable with the collet seat and is actuatable between provisionally locked and locked configurations, wherein each of the compressible collet, collet seat and compression nut are generally cylindrical and when assembled share a common center axis, and wherein the compressible collet is engageable and compressible directly with the coupling component, wherein engagement between the components is achieved by one of press fitting and threaded engagement between the collet seat and the compression nut, wherein the toggle is engageable with the coupling component in a cantilever pivotal arrangement, such that in one configuration, the toggle is pivoted into linear alignment with the coupling component and is nested within a recess therein, and in a second configuration, the toggle is deployed in a generally perpendicular orientation relative to the axis of the coupling component, and wherein the engagement between the locking assembly is by threaded engagement between the collet seat comprising interior threads and a threaded compression nut comprising corresponding threads for engagement with the collet seat, wherein at least one of (i) at least a portion of an outer surface of the distal end of the coupling component and (ii) at least a portion of an inner face of the compressible collet comprises a surface feature selected from one or a combination of ridges, grooves, keels, fins, threads, dimples, knurls, and surface texturing, and wherein the surface features of the at least one of the outer surface of the coupling component and the inner face of the compressible collet cooperate with the opposing surface of the assembly when the locking assembly is in a locked configuration to enhance the compressive securement of the locked compression fixture system, wherein each of the at least a portion of an outer surface of the distal end of the coupling component and at least a portion of an inner face of the compressible collet comprises a surface feature, wherein the compressible collet is selected from (i) unitary slit form that comprises at least one slit selected from a through slit and a partial slit, and (ii) a multi piece form, and wherein the inner sleeve of the insertion tool engages with the nut and the outer sleeve engages with the collet seat, and wherein upon engagement of the sleeves the inner sleeve is actuated by rotation around the shared axis to drive further engagement of the engaged threads of the collet seat and the nut in a distal direction to lock the nut to the collet seat and thereby compress and lock the compressible collet into compressive engagement with the coupling component.

18. A compression fastener system according to claim 1, wherein the compression component comprises a securement ring that operates to retain the compressible collet in a first configuration to provisionally secure the locking assembly to the coupling component and in a second configuration to fixedly secure the locking assembly into compression locking with the coupling component, wherein each of the compressible collet and the securement ring are generally cylindrical, and wherein the compressible collet is engageable and compressible directly with the coupling component, and wherein when the locking assembly and the coupling component are assembled they share a common center axis, and wherein engagement between the components is achieved by press fitting, wherein, the securement ring comprises a contractile material that is responsive to application of an activator selected from one or more of heat, electrical, chemical and mechanical compressive force such that in a pre activated form, the ring is either or both pliable and has a circumferential dimension that is greater than the receiving recess of the compressible collet, and in the activated form the ring is contracted so that it becomes more rigid and contracts to assume a smaller circumferential diameter such that it fits within and compresses against the compressible collet thereby locking the assembly to the coupling component.

19. A compression fastener system comprising:
- a coupling component having proximal and distal ends and an elongate axis,
- a toggle anchor affixed to the distal end of the coupling component, the toggle anchor being pivotal around an axis that is perpendicular to the elongate axis of the coupling component, and
- a locking assembly that is engageable with the coupling component in a co-axial orientation around the elongate axis of the coupling component, the locking assembly comprising a compressible collet and a collet compression component.

20. A compression fastener system according to claim 19, wherein the coupling component is selected from a wire and a bone pin.

21. A compression fastener system according to claim 19, wherein the collet compression component is selected from (i) a locking cap that is engagable with the compressible collet, and (ii) a seat for retaining the compressible collet, and a compression nut that is engagable with the seat.

22. A compression fastener system according to claim 21, wherein the collet compression component is a locking cap that is engagable with the compressible collet and further comprises a flexible securement ring that is engageable circumferentially on an outer surface of the compressible collet, the locking cap being further engageable with the securement ring.

23. A compression fastener system according to claim 22, wherein the coupling component is a wire that comprises flexible metal, and wherein the compressible collet comprises on its outer surface a circumferential recess for retaining the flexible securement ring.

24. A method for achieving compression fixation of a plurality of bone elements, comprising:
- inserting an elongate coupling component having distal and proximal ends into a through hole in each of the bone elements, the bone elements arranged for fixation along a generally linear path from a proximal position to a distal position,
- actuating an anchor at the distal end of the coupling component into engagement with a distal face of the most distally positioned bone element,
- sequentially engaging each of a locking assembly, and tensioning and insertion tools into engagement with the coupling component, the tensioning tool engaged fixedly with the proximal end of the coupling component and also engaged loosely with a more distal portion of the coupling component; each of the locking assembly and the insertion tool engaged along an axis that is shared with the coupling component, the insertion tool positioned between a more distal engagement position of the tensioning tool and the most proximally positioned fragment of the aligned bone fragments, and the locking assembly positioned between the insertion tool and the most proximally positioned fragment of the aligned bone fragments,
- actuating the tensioning tool to displace the coupling component in a proximal direction thereby exerting distally directed pressure on the insertion tool whereby distally directed pressure is also exerted on the locking assembly to direct the locking assembly into compressive contact with the most proximally positioned fragment, and
- actuating the insertion tool to engage the locking assembly into a locked configuration.

* * * * *